(12) United States Patent
Robertson et al.

(10) Patent No.: US 8,067,368 B2
(45) Date of Patent: Nov. 29, 2011

(54) VASCULAR ENDOTHELIAL GROWTH FACTORS AND METHODS OF THEIR USE

(75) Inventors: Fredika Robertson, Dublin, OH (US); John Bauer, Columbus, OH (US)

(73) Assignees: The Ohio State University Research Foundation, Columbus, OH (US); Nationwide Children's Hospital, Inc., Columbus, OH (US)

(*) Notice: Subject to any disclaimer, the term of this patent is extended or adjusted under 35 U.S.C. 154(b) by 601 days.

(21) Appl. No.: 10/597,509

(22) PCT Filed: Jan. 27, 2005

(86) PCT No.: PCT/US2005/002929
§ 371 (c)(1),
(2), (4) Date: Aug. 20, 2008

(87) PCT Pub. No.: WO2005/072417
PCT Pub. Date: Aug. 11, 2005

(65) Prior Publication Data
US 2008/0299167 A1    Dec. 4, 2008

Related U.S. Application Data

(60) Provisional application No. 60/539,852, filed on Jan. 27, 2004.

(51) Int. Cl.
*A61K 38/18* (2006.01)
*C07K 14/475* (2006.01)

(52) U.S. Cl. .......... 514/8.1; 530/399; 606/228; 606/231

(58) Field of Classification Search .................. None
See application file for complete search history.

(56) References Cited

U.S. PATENT DOCUMENTS

| | | |
|---|---|---|
| 4,373,217 A | 2/1983 | Draenert |
| 5,011,912 A | 4/1991 | Hopp et al. |
| 5,545,806 A | 8/1996 | Lonberg et al. |
| 5,569,825 A | 10/1996 | Lonberg et al. |
| 6,140,073 A | 10/2000 | Bayne et al. |
| 2003/0114366 A1 | 6/2003 | Martin et al. |

FOREIGN PATENT DOCUMENTS

WO    2005072417 A2    8/2005

OTHER PUBLICATIONS

Claffey, et al. "Vascular Endothelial Growth Factor", The Journal of Biological Chemistry (1992), vol. 267, No. 23, pp. 16317-16322.
Cui, et al. "Differentiated human podocytes endogenously express an inhibitory isoform of vascular endothelial growth factor (VEGF165b) mRNA and protein", Am. J. Physiol Renal Physiol. (2004), vol. 286, No. 4, pp. F767-F773.
Ferrara, "Vascular Endothelial Growth Factor", European J. of Cancer (1996), vol. 52A, No. 14, pp. 2413-2422.
Grunstein, et al. "Isoforms of Vascular Endothelial Growth Factor Act in a Coordinate Fashion to Recruit and Expand Tumor Vasculature", Molecular and Cellular Biology (2000), vol. 20, No. 19, pp. 7282-7291.
Hopp, et al. "A Short Polypeptide Marker Sequence Useful for Recombinant Protein Identification and Purification", Bio/Technology (1988), vol. 6, pp. 1204-1210.
Ito, et al. "Hair follicle stem cells in the lower bulge form the secondary germ, a biochemically distinct but functionally equivalent progenitor cell population, at the termination of catagen", Differentiation (2004), vol. 72, pp. 548-557.
Larrick, et al. "Polymerase Chain Reaction Using Mixed Primers: Cloning of Human Monoclonal Antibody Variable Region Genes from Single Hybridoma Cells", Bio/Technology (1989), vol. 7, p. 934-938.
Liu, et al. "Chimeric Mouse-Human IgG1 Antibody that Can Mediate Lysis of Cancer Cells Chimeric Mouse-Human IgG1 Antibody that Can Mediate Lysis of Cancer Cells", PNAS (1987), vol. 84, pp. 3439-3443.
Maniatis, et al. "Molecular Cloning (A Laboratory Manual)", Cold Spring Harbor Laboratory (1982), pp. 387-389.
Mihm, et al. "Intracellular distribution of peroxynitrite during doxorubicin cardiomyopathy: evidence for selective impairment of myofibrillar creatine kinase", Br. J. Pharmacol. (2002), vol. 135, No. 3, pp. 581-588.
Needleman, et al. "A general method applicable to the search for similarities in the amino acid sequence of two proteins", J. Mol. Bio. (1970), vol. 48, pp. 443-453.
International Search Report for WO 2005/072417 (PCT/US2005/002929), mailed Feb. 4, 2009.
Written Opinion for WO 2005/072417 (PCT/US2005/002929), mailed Feb. 20, 2009.
International Preliminary Report on Patentability for WO 2005/072417 (PCT/US2005/002929), mailed Feb. 24, 2009.
Affara, et al. "Vascular Endothelial Growth Factor as a Survival Factor in Tumor-Associated Angiogenesis", in vivo, (2004), vol. 18, pp. 525-542.
Bates, et al. "VEGF165b, an Inhibitory Splice Variant of Vascular Endothelial Growth Factor, Is Down-Regulated in Renal Cell Carcinoma", Cancer Research, (2002), vol. 62, No. 14, pp. 4123-4131.
Bates, et al. "VEGF165b, an Inhibitory Vascular Endothelial Growth Factor Splice Variant Mechanism of Action, In vivo Effect on Angiogenesis and Endogenous Protein Expression", Cancer Research (2004), vol. 64, No. 21, pp. 7822-7835.
Borgstrom, et al. "Importance of VEGF for breast cancer angiogenesis in vivo: implications from intravital microscopy of combination treatments with an anti-VEGF neutralizing monoclonal antibody and doxorubicin", Anticancer Research (1999), vol. 19, No. 5B, pp. 4203-4214.
Ortiz, et al. "Mesenchymal stem cell engraftment in lung is enhanced in response to bleomycin exposure and ameliorates its fibrotic effects", PNAS (2003), vol. 100, No. 14, pp. 8407-8411.
Ozerdem, et al "Early Contribution of Pericytes to Angiogenic Sprouting and Tube Formation", Angiogenesis (2003), vol. 6, No. 3, pp. 241-249.

(Continued)

*Primary Examiner* — Christine J Saoud
(74) *Attorney, Agent, or Firm* — Calfee, Halter & Griswold LLP

(57) ABSTRACT

Vascular endothelial growth factor alternative splice variants and methods of their use are provided.

8 Claims, 13 Drawing Sheets

OTHER PUBLICATIONS

Riechmann, et al. "Reshaping human antibodies for therapy", Nature (1988), vol. 332, pp. 323-327.

Robertson, et al. "Gene expression and cellular sources of inducible nitric oxide synthase during tumor promotion", Carcinogenesis (1996), vol. 17, No. 9, pp. 2053-2059.

Robinson, et al. "The splice variants of vascular endothelial growth factor (VEGF) and their receptors", J. of Cell Science (2001), vol. 114, No. 5, pp. 853-865.

Song, et al. "Angiogenic role for glycodelin in tumorigensis", PNAS (2001), vol. 96, No. 16, pp. 9265-9270.

Sugihara, et al. "A Novel Alternatively Spliced Form of murine Vascular Endothelial Growth Factor, VEGF 115*", The Journal of Biological Chemistry (1998), vol. 273, No. 5, pp. 3033-3038.

Tober, et al. "Comparative Expression of Novel Vascular Endothelial Growth FactorNascular Permeability Factor Transcripts in Skin, Papillomas, and Carcinomas of v-Ha-ras Tg.AC Transgenic Mice and FVB/N Mice", Biochemical and Biophysical Research Communications (1998), vol. 247, pp. 644-653.

Trempus, et al. "Enrichment for Living Murine Keratinocytes from the Hair Follicle Bulge with the Cell Surface Marker CD34", J. Invest. Dermatol. (2003), vol. 120, pp. 501-511.

Weinstein, et al. "Cardiac Peroxynitrite Formation and Left Ventricular Dysfunction following Doxorubicin Treatment in Mice", J. Pharmacol. Exp. Ther. (2000), vol. 294, No. 1, pp. 396-401.

Winter, et al. "Humanized antibodies", TIPS (1993), vol. 14, pp. 139-143.

Woolard, et al. "VEGF165b, an Inhibitory Vascular Endothelial Growth Factor Splice Variant: Mechanism of Action, In vivo Effect On Angiogenesis and Endogenous Protein Expression", Cancer Research (2004), vol. 64, No. 21, pp. 7822-7835.

Zhang, et al. "Tracking angiogenesis induced by skin wounding and contact hypersensitivity using a Vegfr2-luciferase transgenic mouse", Blood (2004), vol. 103, No. 2, pp. 617-626.

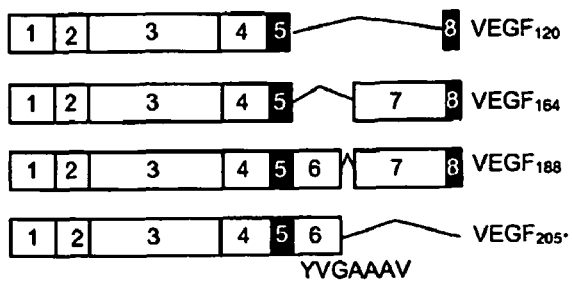
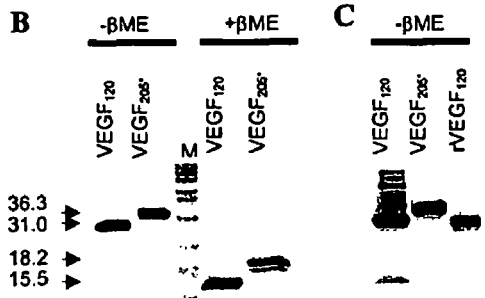
FIGURE 1

*, p<0.05 versus 10μM DOX alone

†, p<0.05 versus equimolar VEGF 120

VEGF 205: M N F L L S W V H W T L A L L L Y L H H A K W S Q A A P T T E G E Q K S H E V I
VEGF 188: M N F L L S W V H W T L A L L L Y L H H A K W S Q A A P T T E G E Q K S H E V I
VEGF 164: M N F L L S W V H W T L A L L L Y L H H A K W S Q A A P T T E G E Q K S H E V I
VEGF 144: M N F L L S W V H W T L A L L L Y L H H A K W S Q A A P T T E G E Q K S H E V I
VEGF 120: M N F L L S W V H W T L A L L L Y L H H A K W S Q A A P T T E G E Q K S H E V I

VEGF 205: K F M D V Y Q R S Y C R P I E T L V D I F Q E Y P D E I E Y I F K P S C V P L M
VEGF 188: K F M D V Y Q R S Y C R P I E T L V D I F Q E Y P D E I E Y I F K P S C V P L M
VEGF 164: K F M D V Y Q R S Y C R P I E T L V D I F Q E Y P D E I E Y I F K P S C V P L M
VEGF 144: K F M D V Y Q R S Y C R P I E T L V D I F Q E Y P D E I E Y I F K P S C V P L M
VEGF 120: K F M D V Y Q R S Y C R P I E T L V D I F Q E Y P D E I E Y I F K P S C V P L M

VEGF 205: R C A G C C N D E A L E C V P T S E S N I T M Q I M R I K P H Q S Q H I G E M S
VEGF 188: R C A G C C N D E A L E C V P T S E S N I T M Q I M R I K P H Q S Q H I G E M S
VEGF 164: R C A G C C N D E A L E C V P T S E S N I T M Q I M R I K P H Q S Q H I G E M S
VEGF 144: R C A G C C N D E A L E C V P T S E S N I T M Q I M R I K P H Q S Q H I G E M S
VEGF 120: R C A G C C N D E A L E C V P T S E S N I T M Q I M R I K P H Q S Q H I G E M S

VEGF 205: F L Q H S R C E C R P K K D R T K P E K K S V R G K G K G Q K R K R K K S R F K
VEGF 188: F L Q H S R C E C R P K K D R T K P E K K S V R G K G K G Q K R K R K K S R F K
VEGF 164: F L Q H S R C E C R P K K D R T K P E N H G E P C S E R R K H L F V Q D P Q T C
VEGF 144: F L Q H S R C E C R P K K D R T K P E K K S V R G K G K G Q K R K R K K S R F K
VEGF 120: F L Q H S R C E C R P K K D R T K P E

VEGF 205: S W S V
VEGF 188: S W S V
VEGF 164: K C S C K N T D S R C K A R Q L E L N E R T C R C D K P R R
VEGF 144: S W S V

VEGF 188:

FIGURE 6

```
ATG AAC TTT CTG CTG TCT TGG GTG CAC TGG ACC CAG GCT TTG  42
 M   N   F   L   L   S   W   V   H   W   T   Q   A   L   14
CTG GTG TAC CTG CAG GAT GGG AAG TGG TCG CAG GCT GCA CCC ACG ACA GAA GGA GAG CAG 102
 L   V   Y   L   H   H   A   K   W   S   Q   A   P   T   T   E   G   E   Q   34

AAG TCC CAT GAA GTG ATC AAG TTC ATG GAT GTC TAC CAG CGA AGC TAC TGC CGT CCG ATT 162
 K   S   H   E   V   I   K   F   M   D   V   Y   Q   R   S   Y   C   R   P   I   54

GAG ACC CTG GTG GAC ATC TTC CAG GAG TAC CCC GAC GAG ATA GAG TAC ATC TTC AAG CCG 222
 E   T   L   V   D   I   F   Q   E   Y   P   D   E   I   E   Y   I   F   K   P   74

TCC TGT GTG CCG CTG ATG CGC TGT GCA GGC TGT TGT AAC GAT GAA GCC CTG GAG TGC GTG 282
 S   C   V   P   L   M   R   C   A   G   C   C   N   D   E   A   L   E   C   V   94

CCC ACG TCA GAG AGC AAC ATC ACC ATG CAG ATC ATG CGG ATC AAA CCT CAC CAA AGC CAG 342
 P   T   S   E   S   N   I   T   M   Q   I   M   R   I   K   P   H   Q   S   Q   114

CAC ATA GGA GAG ATG AGC TTC CTA CAG CAC AGC AGA TGT GAA TGC AGA CCA AAG AAA GAC 402
 H   I   G   E   M   S   F   L   Q   H   S   R   C   E   C   R   P   K   K   D   134

AGA ACA AAG CCA GAA AAA AAA TCA GTT CGA GGA AAG GGA AAG GGT CAA AAA CGA AAG CGC 462
 R   T   K   P   E   K   K   S   V   R   G   K   G   K   G   Q   K   R   K   R   154

AAG AAA TCC CGG TTT AAA TCC TGG AGC GTG TAC GTT GGT GCC GCT GCT GTC TAA TTC CTT 522
 K   K   S   R   F   K   S   W   S   V   Y   V   G   A   A   A   V   *           174
```

FIGURE 7

VASCULAR ENDOTHELIAL GROWTH FACTORS AND METHODS OF THEIR USE

This application claims priority to U.S. Provisional Application No. 60/539,852, filed Jan. 27, 2004 the entire disclosure of which is incorporated herein by reference.

This invention was supported, at least in part, by Grant HL 69693 from the National Heart, Lung & Blood Institute. The U.S. government has certain rights in the invention.

FIELD OF THE INVENTION

The present invention relates to vascular endothelial growth factor (VEGF) alternative splice variants, including $VEGF_{205*}$. These variants can be used in numerous clinical treatments and can be used for experimental purposes.

BACKGROUND OF THE INVENTION

Vascular endothelial growth factor A/vascular permeability factor (VEGF A/VPF) is a complete pro-angiogenic growth factor that increases permeability of microvessels, stimulates endothelial cell proliferation, migration, and differentiation into tubules, which are precursors to blood vessels. In addition, it can also serve as a survival factor that protects vascular endothelial cells against apoptosis and senescence.

Although one gene encodes for rodent and human VEGF-A, a number of VEGF-A proteins with specific activities can be produced through alternative splicing of the eight exons within the single VEGF gene. In humans, seven different alternative splice variants of VEGF have been identified thus far. In the murine system, five alternative splice variants have been identified, which are one amino acid shorter than those in the human system.

The splice variants of murine VEGF thus far identified are designated as $VEGF_{120}$, $VEGF_{144}$, $VEGF_{164}$, and $VEGF_{188}$. The basis for the different biological functions of VEGF splice variants is based on the specific exons present in the mRNA of the splice variant that determines the amino acids present and in turn determines the differences in the binding and affinity of the VEGF-A splice variants for the VEGF receptors, which include the receptor tyrosine kinases VEGFR-1, VEGFR-2, and the co-receptors, neuropilin-1 (NP-1) and NP-2. Endothelial cell proliferation is stimulation through phosphorylation of VEGFR-2 (Flk-1/KDR).

The existence of a novel VEGF alternative splice transcript was previously reported, and designated $VEGF_{205}$. That variant was present only in mouse skin papillomas and squamous cell carcinomas, but not in normal skin. In this specification, we describe for the first time the cloning, sequencing, and characterization of a new VEGF, $VEGF_{205*}$, a 145-amino acid protein with significantly different carboxyl-terminus tail than any other VEGF alternative splice variant described to date in mouse or human systems.

SUMMARY OF THE INVENTION

In accordance with the invention, novel VEGF alternative splice variant polypeptides are provided. Also provided are nucleic acid sequences coding for those polypeptides, antibodies to the polypeptides, and methods of using all of the foregoing.

The invention provides isolated or purified polypeptides comprising the 145-amino acid sequence set forth in FIG. 7. Also provided are isolated or purified polypeptides consisting of the 145-amino acid sequence set forth in FIG. 7. Also provided are isolated or purified polypeptides comprising the 171-amino acid sequence, which includes a 26-amino acid signal sequence, set forth in FIG. 7.

In other embodiments, the invention provides an isolated or purified polypeptide comprising the amino acid sequence YVGAAAV (SEQ ID NO: 16), wherein the polypeptide stimulates a protein kinase B signaling pathway. The protein kinase B can be Akt. In some embodiments, the polypeptide binds vascular endothelial growth factor receptor-2. The endothelial growth factor receptor-2 can be flk-1/KDR.

The invention also provides methods of inducing migration and/or organization and/or survival of vascular endothelial cells, comprising administering an effective amount of a polypeptide of the invention. Also provided are methods of attenuating chemotherapy toxicity in a patient receiving chemotherapy, comprising administering a toxicity attenuating amount an inventive polypeptide. The chemotherapy can comprise administration of doxorubicin, and the toxicity can comprise a toxicity chosen from toxicity to cardiac tissue, bone marrow, gastrointestinal tract, kidney, and bladder. The invention also provides methods of preventing or attenuating damage to stem cells resulting from chemotherapy or other cytotoxic agents or treatments.

The invention also provides methods of lengthening the life-span of living tissue outside of a living being, comprising applying to the tissue an effective amount of a polypeptide of the invention. In some embodiments, the tissue is organ tissue. The invention also provides methods of protecting against ischemic reperfusion injury, comprising administering an effective amount of a polypeptide of the invention to a patient anticipated to suffer ischemic reperfusion injury. The administration can be targeted to a tissue anticipated to suffer ischemic reperfusion injury. The administration is performed during a surgical procedure, prior to surgical wound closure, and the tissue is chosen from lung, carotid artery, aorta, and cardiac tissue.

The invention also provides implantable medical devices or implants coated with a polypeptide of the invention. The device or implant can be a suture.

In still other embodiments, the invention provides methods of increasing the rate of wound healing, comprising applying to a wound in need of healing an effective amount of a vascular endothelial growth factor (VEGF) variant. The VEGF variant can comprise a variant chosen from $VEGF_{144}$, $VEGF_{164}$, and a polypeptide of the invention. In some embodiments, the wound in need of healing is chosen from diabetic ulcers, ulcers resulting from peripheral arterial disease, pressure sores, acute surgical wounds, and burns.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIG. 1A illustrates the exon structure of the commonly expressed $VEGF_{120}$ alternative splice variant compared to VEGF$_{164}$, VEGF$_{188}$, and the novel VEGF$_{205*}$ alternative splice variant. In the Figure, boxes represent exons. VEGF$_{205*}$ is encoded by exons 1-5 and contains an extended exon 6 spliced to a site that is 5' of exon 7. Exon 6 of VEGF$_{205*}$ encodes a unique 7-amino acid carboxyl-terminal tail, YVGAAAV (SEQ ID NO: 16), that is significantly different from the carboxyl-terminal tail of other VEGF alternative splice variants that have been identified.

FIG. 1B illustrates the expression and refolding of recombinant VEGF$_{205*}$. Recombinant VEGF$_{205*}$ and VEGF$_{120}$ were purified from overexpressing E. coli and refolded into homodimers. The purified refolded proteins (600 ng) were separated on a 12% SDS-PAGE gel under non-reducing (−beta-mercaptoethanol; −βME) conditions to show VEGF dimer formation and under reducing (+βME) conditions to show monomer formation. The gel was Commassie-blue stained and photographed. Arrowheads indicate the position of recombinant VEGF proteins. Size marker is indicated as (M).

FIG. 1C shows a Western blot of purified recombinant VEGF splice variants. Aliquots of 200 ng of purified recombinant VEGF splice variants were separated on a 12% SDS-PAGE gel and blotted onto nitrocellulose membrane. Recombinant VEGF$_{205*}$ and VEGF$_{120}$ were detected using a polyclonal VEGF antibody directed against VEGF$_{164}$. To confirm the position of purified recombinant VEGF proteins, a commercially available recombinant VEGF$_{120}$ (rVEGF$_{120}$) (R&D Systems) was used as a positive control.

FIG. 6 shows an amino acid sequence alignment of the VEGF alternative splice variant sequences for VEGF$_{205*}$ (SEQ ID NO: 1), VEGF$_{188}$ (SEQ ID NO: 2), VEGF$_{164}$ (SEQ ID NO: 3), VEGF$_{144}$ (SEQ ID NO: 4), and VEGF$_{120}$ (SEQ ID NO: 5). The murine VEGF isoforms are aligned to show how they differ at their amino termini (shaded sequences).

FIG. 7 shows a comparative cDNA sequence (SEQ ID NO: 6) and amino acid sequence (SEQ ID NO: 1) of murine VEGF$_{205*}$ isoform. The highlighted area shows the signal sequence of 78 nucleotides and 26 amino acids. The entire sequence of VEGF is 171 amino acids—the signal sequence of 26 amino acids is cleaved from the mature VEGF$_{205*}$ polypeptide. The presence of the stop codon TAA results in a truncated protein of 145 amino acids. Numbering of the nucleotide and amino acid sequence for murine VEGF$_{205*}$ is shown.

DESCRIPTION OF EMBODIMENTS

The present invention will now be described, with occasional reference to the accompanying drawings in which specific embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Polypeptides and Fragments Thereof

Figure 8:
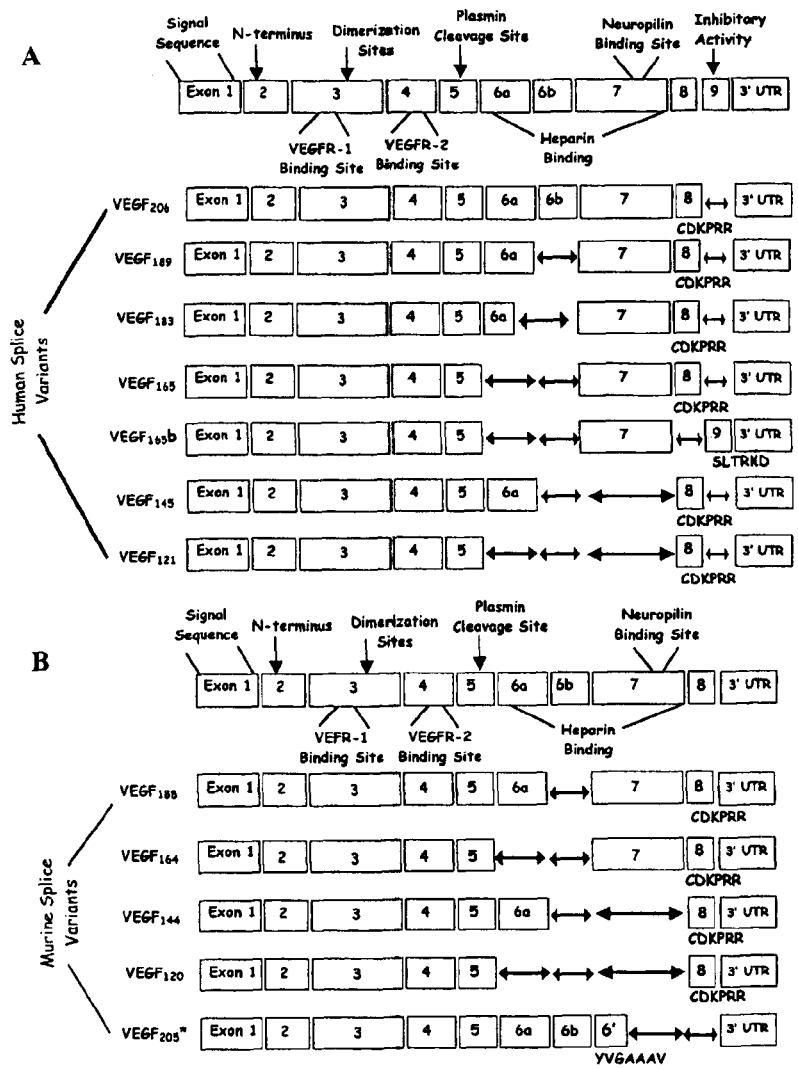
FIG. 8 illustrates gene structures for human and murine alternative splice variants.

The present invention is based on the discovery of a new alternative splice variant of the VEGF protein. This novel protein has 145 amino acids and ends in a carboxyl terminal sequence that is different from all other VEGF alternative splice variants identified to date. (FIG. 8 illustrates gene structure of human and murine alternative splice variants.) The novel protein is referred to herein as VEGF$_{205*}$ and the gene sequence encoding the protein has been called VEGF205*. The nucleic acid sequence was identified as being from the same locus as other known VEGF variants, and it was concluded that the variant is not encoded from a different gene than the known VEGF, but is the result of alternative splicing.

Thus, in one aspect of the invention, a novel isolated or purified polypeptide is presented. The polypeptide comprises the amino acid sequences set forth in FIG. 7. These sequences encompass the 171-amino acid sequence including the signal sequence, and the 145-amino acid sequence lacking the signal sequence. Thus, polypeptides with and without a signal sequence are contemplated. The invention further encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

The polypeptides of the invention include full length proteins encoded by the nucleic acid sequence set forth in FIG. 7. Like the amino acid sequences above, these sequences include nucleic acid sequences coding for polypeptides with and without a signal sequence. In some embodiments of the invention, polypeptides comprise the amino acid sequence set forth in FIG. 7. Of course, additional amino acids can be added to the carboxyl and/or amino terminus of the polypeptide without departing from the scope of the invention. In some embodiments, the polypeptide consists of the sequences set forth in FIG. 7.

Also provided herein are polypeptide fragments comprising at least 3, 4, 5, 6, 7, 8, 9, 10, 11, 12, 13, 14, 15, 16, 17, 18, 19, 20, 30, 40, 50, 60, 70, 80, 90, 100, 110, 120, 130, or 140 or more contiguous amino acids, or any whole number in between, of the sequences shown in FIG. 7.

The polypeptides of the invention can be monomeric or dimeric. The polypeptides of the invention can be membrane bound or they can be secreted and thus soluble.

Also contemplated and provided are naturally occurring variants, as well as derived variants of the polypeptides and fragments provided herein. Variants may exhibit amino acid sequences that are at least 80%, 85%, 90%, 91%, 92%, 93%, 94%, 95%, 96%, 97%, 98%, 99%, or greater percent identical to the sequences shown in FIG. 7. Percent identity may be determined by visual inspection and mathematical calculation. Alternatively, the percent identity of two protein sequences can be determined by comparing sequence information using the GAP computer program, based on the algorithm of (Needleman and Wunsch, J. Mol. Bio., 48:443 (1970)) and available from the University of Wisconsin Genetics Computer Group (UWGCG). Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups, etc. Covalent derivatives can be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Fusion proteins can comprise peptides added to facilitate purification and identification. Such peptides include, for example, poly-His or the antigenic identification peptides described in U.S. Pat. No. 5,011,912 and in (Hopp et al., Bio/Technology, 6:1204 (1988)).

Among the variant polypeptides provided herein are variants of native polypeptides that retain the native biological activity or the substantial equivalent thereof. One example is a variant that binds with essentially the same binding affinity as does the native form.

Variants include polypeptides that are substantially homologous to the native form, but which have an amino acid sequence different from that of the native form because of one or more deletions, insertions, or substitutions. Particular embodiments include, but are not limited to, polypeptides that comprise from one to ten deletions, insertions or substitutions of amino acid residues, when compared to the sequences shown in FIG. 7.

An amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; and substitutions of one aromatic residue for another, such as Phe, Trp, or Tyr for one another. Other conservative substitutions, e.g., involving substitutions of entire regions having similar hydrophobicity characteristics, are well known. Of course, non-conservative substitutions can also be made, if desired.

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one embodiment, the purification of recombinant polypeptides or fragments can be accomplished using fusions of polypeptides or fragments of the invention to another polypeptide to aid in the purification of polypeptides or fragments of the invention.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification, or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix, or substrate having pendant diethylaminoethyl (DEAE) groups. The matrices can be acrylamide, agarose, dextran, cellulose, or other types commonly employed in protein purification. Alternatively, a cation exchange step can be employed. Suitable cation exchangers include various insoluble matrices comprising sulfopropyl or carboxymethyl groups.

In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and/or purified protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method can be useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

The desired degree of purity depends on the intended use of the protein. A relatively high degree of purity may be desired when the polypeptide is to be administered in vivo, for example. In such a case, the polypeptides can be purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Commassie blue staining, or if the protein is radiolabeled, by autoradiography.

Antibodies that are immunoreactive with the polypeptides of the invention are provided herein. Such antibodies specifically bind to the polypeptides, or fragments, variants, fusion-proteins thereof, etc., via antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc., contain antigenic determinants or epitopes that elicit the formation of antibodies.

These antigenic determinants or epitopes can be linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9, Garland Publishing Inc., 2nd ed. (1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14, Garland Publishing Inc., 2nd ed. (1996)). Epitopes may be identified by any of the methods known in the art.

Another aspect of the present invention relates to the antigenic epitopes of the polypeptides of the invention. Such epitopes are useful for raising antibodies, in particular monoclonal antibodies. Additionally, epitopes from the polypeptides of the invention can be used as research reagents, in assays, including but not limited to ELISA and EIA, and to purify specific binding antibodies from substances such as polyclonal sera, from for example, sheep, rabbits, pigs, or chicken, or supernatants from cultured hybridomas. Such epitopes or variants thereof can be produced using techniques well known in the art such as solid-phase synthesis, chemical or enzymatic cleavage of a polypeptide, or using recombinant DNA technology. The polypeptides (and fragments and/or variants) can be labeled, such as with a fluorescent or radio-label, to identify associated receptors or binding proteins. Assays and research tools in which the present invention can be used will be immediately apparent to one of ordinary skill in the art.

As to the antibodies that can be elicited by the epitopes of the polypeptides of the invention, whether the epitopes have been isolated or remain part of the polypeptides, both polyclonal and monoclonal antibodies can be prepared by conventional techniques. See, for example, (Kennet et al., Monoclonal Antibodies, Hybridomas: A New Dimension in Biological Analyses, eds., Plenum Press, N.Y. (1980); and Harlow and Land, Antibodies: A Laboratory Manual, eds., Cold Spring Harbor Laboratory Press, Cold Spring Harbor, N.Y., (1988)).

Hybridoma cell lines that produce monoclonal antibodies specific for the polypeptides of the invention are also specifically contemplated as being within the scope of this invention. Such hybridomas can be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies can be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen-binding site thereof) and a constant region derived from a human antibody. Alternatively, a humanized antibody fragment can comprise the antigen-binding site of a murine monoclonal antibody and a variable region fragment (lacking the antigen-binding site) derived from a human antibody. Procedures for the production of chimeric and further engineered monoclonal antibodies include those described in (Riechmann et al., Nature 332: 323 (1988), Liu et al., PNAS 84:3439 (1987), Larrick et al., Bio/Technology 7:934 (1989), and Winter and Harris, TIPS 14:139 (May 1993)). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which can be produced by conventional techniques, are also encompassed by the present invention. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

The antibodies of the present invention, and in particular, the humanized antibodies of the present invention, can be used in the treatment of cancer and in the prophylaxis of metastasis. Antibodies of the invention can also be used in treating endometriosis, keloid scarring, psoriasis, and autoimmune diseases, including but not limited to systemic lupus and multiple sclerosis.

Nucleic Acid Sequences

The present invention also includes nucleic acid sequences, including those shown in FIG. 7, which code for polypeptide (including fragments and variants thereof) sequences of the present invention. Like the amino acid sequences described above, the nucleic acid sequences of the invention include variants that differ from a native sequences because of one or more deletions, insertions, or substitutions, but that encode a biologically active polypeptide.

The present invention further provides nucleic acid sequences comprising or consisting of sequences that encode the inventive amino acid sequences, including the fragments and variants of the amino acid sequences. Due to the degenerative nature of the genetic code, a plurality of alternative nucleic acid sequences, can code for the amino acid sequences of the invention. Those alternative nucleic acid sequences are also expressly contemplated as being within the scope of the present invention.

The present invention further provides expression vectors and cloning vectors comprising any of the above nucleic acid sequences, as well as host cells transfected by said vectors.

Another aspect of the invention is DNA sequences coding for expression of a polypeptide of the invention. Such sequences include the sequences of nucleotides in a 5' to 3' direction illustrated in FIG. 7, DNA sequences which, but for the degeneracy of the genetic code, are identical to the DNA sequences illustrated in FIG. 7, and encode the proteins of FIG. 7. Further included in the present invention are DNA sequences that hybridize under stringent conditions with the DNA sequences of FIG. 7 and encode a VEGF protein. Examples of DNA sequences include those that hybridize under stringent conditions (see, T. Maniatis et al, Molecular Cloning (A Laboratory Manual), Cold Spring Harbor Laboratory (1982), pages 387 to 389). Such DNA sequences can encode a polypeptide that is at least about 70%, 80%, 90%, or even higher percent homologous, to the polypeptides shown in FIG. 7. Finally, allelic or other variations of the sequences shown in FIG. 7, whether such nucleotide changes result in changes in the peptide sequence or not, but where the peptide sequence still has VEGF activity, are also included in the present invention. The present invention also includes fragments of the DNA sequences shown in FIG. 7, which encode a polypeptide retaining the activity of a VEGF protein.

While not wishing to be bound by any particular theory, it is believed that $VEGF_{205*}$ acts as a survival factor through IP3-K/Akt. It is believed that this activity occurs through Ser 473 as opposed to Thr 308. The survival factor activity of $VEGF_{205*}$ allows it to be used in inducing survival of stem cells, and as an additive to stem cell culture media. Other embodiments of the invention include cell culture media that include $VEGF_{205*}$.

Pharmaceutical Compositions and Treatments

The present invention still further provides pharmaceutical compositions comprising, as an active ingredient, nucleic acid sequences, expression vectors, polypeptides, proteins, fragments, or variants of any of the foregoing.

Throughout the specification, reference is made to polypeptides and proteins of the invention, in some embodiments in which amino acids are mutated by, for example, deletion or substitution. It should be noted that other modifications of the inventive polypeptides and proteins are specifically contemplated as well. For example, modifications to change the pharmacokinetic profile of the inventive compounds, or to otherwise modify their physicochemical characteristics, such as through the use of pegylation, lipidation, glycosylation, phosphorylation, or any other chemical (including peptide and nucleic acid) addition, are specifically contemplated. Examples of methods for achieving such modifications are well known to those of ordinary skill in the art.

The pharmaceutical compositions of the invention can be administered using those methods currently used to administer VEGFs or other angiogenic factors.

The pharmaceutical compositions can be orally administered, for example, with an inert diluent or with an edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of the active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain one or more of the following pharmaceutically acceptable excipients: a binder, such as gum tragacanth, acacia, cornstarch, or gelatin; dicalcium phosphate; a disintegrating agent, such as corn starch, potato starch, alginic acid and the like; a lubricant, such as magnesium stearate; a sweetening agent, such as sucrose, lactose, or saccharin; and/or a flavoring agent, such as peppermint, oil of wintergreen, or cherry flavoring. Examples of other pharmaceutically acceptable excipients are well known to those of ordinary skill.

When the dosage unit form is a capsule, it may contain, in addition to materials of the above type, a liquid carrier. Various other materials may be present as coatings or otherwise to modify the physical form of the dosage unit. For instance, tablets, pills, or capsules may be coated with shellac, sugar, or both. A syrup or elixir may contain the active compounds sucrose as a sweetening agent methyl and propylparabens as preservatives, a dye, and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds can also be administered parenterally or intraperitoneally. Solutions of the active compounds can be prepared in water suitably mixed with a surfactant. Dispersions can also be prepared in glycerol, liquid polyethylene glycols, and mixtures thereof and in oils. Under ordinary conditions of storage and use, these preparations contain a preservative to prevent the growth of microorganisms.

It is also contemplated that the presently described nucleic acid sequences, expression vectors, polypeptides, proteins, fragments, or variants of any of the foregoing, may be formulated as a nasal spray, and used in therapeutically effective doses for the indications described herein.

Sterile injectable solutions can be prepared by incorporating the active compounds in the required amount in the appropriate solvent, optionally, with various of the other ingredients enumerated above, as required, followed by filter sterilization. Generally, dispersions are prepared by incorporating the various sterilized active ingredients into a sterile vehicle which contains the basic dispersion medium and the desired other ingredients from those enumerated above. In the case of sterile powders for the preparation of sterile injectable solutions, the preferred methods of preparation are vacuum-drying and freeze-drying techniques, which yield a powder of the active ingredient plus any additional desired ingredient from a previously sterile-filtered solution thereof.

The inventive nucleic acid sequences, expression vectors, polypeptides, proteins, fragments, or variants of any of the foregoing, in pharmaceutical compositions, are suitable for single administration or in a series of administrations. The administrations can be parenteral, topical, and/or oral administration. Parenteral administration is preferably by intravenous, subcutaneous, intradermal, intraperitoneal, or intramuscular administration. For parenteral administration, the compositions can include active compounds and a suitable sterile carrier such as water, aqueous buffer, 0.4% saline solution, 0.3% glycine, hyaluronic acid or emulsions of non-toxic nonionic surfactants as is well known in the art. The compositions may further include substances to approximate physiological conditions such a buffering agents and wetting agents such as NaCl, KCl, $CaCl_2$, sodium acetate and sodium lactate.

Compositions suitable for parenteral administration also may conveniently comprise a sterile aqueous or oleaginous preparation of nucleic acid sequences, expression vectors, polypeptides, proteins, fragments, or variants of any of the foregoing, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa. The pharmaceutical compositions may conveniently be presented in unit dosage form and may be prepared by any of the methods well-known in the art of pharmacy.

As used herein, "pharmaceutically acceptable" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Methods of Treatment

The present invention provides methods for treatment of various conditions or methods for prophylaxis of various conditions. Examples include, but are not limited to, treatment of conditions in which inducement of vascular endothelial growth is desired, and protection against ischemic reperfusion injury. In other embodiments, the pharmaceutical compositions of the invention are used in increasing the rate of wound healing, for example, in refractory wounds such as those found in diabetic ulcers. In still other embodiments, the compositions are used to extend the life-span of organs or cells to be used in transplantation.

Where a therapeutically or prophylactically effective dose of the inventive pharmaceutical composition is administered to the individual, the composition can be administered as a single dose, or a series of dosages over a period of days, weeks, or even months. As used herein, an effective therapeutic dose is a dose that, empirically, results in a desired therapeutic outcome.

The pharmaceutical compositions, generally speaking, can be administered using any mode that is medically acceptable, meaning any mode that produces the desired activity without causing clinically unacceptable adverse effects. Such modes of administration include parenteral routes (e.g., intravenous, intra-arterial, subcutaneous, intramuscular, mucosal, or infusion), but may also include oral, rectal, topical, nasal, or intradermal routes. Other delivery systems can include time-release, delayed release, or sustained release delivery systems. Such systems can avoid repeated administrations, increasing convenience to the subject and the physician. Many types of delivery systems are available and known to those of ordinary skill in the art.

In the administration of the inventive pharmaceutical compositions described above, drug delivery devices such as infusion pumps may be utilized, or the composition may be administered in the form a denatured pellet, or in a hydrogel, or nano-, or microparticles. A discussion of liposomes, micro- and nanoparticles can be found in Pharmaceutical Journal, Vol 263 No 7060 p 309-318, Aug. 28, 1999 Special Feature, the entire disclosure of which is incorporated herein by reference.

Microparticles and nanoparticles can be prepared in a variety of ways, e.g., by controlled precipitation of polymers solubilized in one of the phases of an emulsion. Precipitation of a polymer out of a solvent takes place on solvent evaporation, leaving particles of the polymer suspended in the residual solvent. Drug-loading then occurs simultaneously with particle formation and the presence of surfactants in the aqueous phase may be used to ensure a small particle size. Microparticles may also be prepared by chemical cross-linking of soluble polymers; nanoparticles may be prepared by polymerization of a monomers in a good solvent for the monomer but a poor solvent for the polymer.

Loading of water-soluble drugs into hydrophobic polymer particle matrices can be enhanced by salting out of the active ingredient with soluble inorganic salts, the formation of lipophilic ion pairs of soluble amine drugs with monalkyl phosphate esters, or by exploiting the ionic attraction between basic amine drugs and the carboxylic groups of polylactic acid co-glycolic acid. Micro- and nanoparticles can be biodegradable or bioerodible. Polylactic acid, polyglycolic acid, poly 1'-hydroxybutyrate, and fibrin are examples of biodegradable polymers used to make drug delivery particles, while the alkyl cyanoacrylates are examples of bioerodible polymers. These solid nanoparticles and microparticles may be used to prepare sustained release parenteral formulations or to achieve drug targeting, some examples of which are discussed below. For the purposes of this discussion, nanoparticles are defined as particulate dispersions having a particle size of between about 10 and 500 nm while microparticles are defined as particulate dispersions having a particle size in excess of 500 nm.

Nanoparticles can range in size from about 10 nm to about 500 nm, or from about 20 nm to about 400 nm, or from about 50 to about 250 nm. The desired size will depend on the application. Similarly, nanoparticles can be formulated from practically any desired substance and the choice of media will depend on the desired application.

Because of their small size, nanoparticles may be injected intravenously and used to target drugs to particular areas of the body. The particles, as with all intravenously injected and non-polymer coated colloidal particulates, can be cleared from the circulation by the liver and spleen. To facilitate drug targeting, in tumor tissue for example, a reticuloendothelial system avoidance (stealth) facility may be incorporated using polyoxyethylene. This may be achieved using block polyoxyethylene copolymers in which the hydrophobic portion of the molecule (e.g., polylactic acid) forms the nanoparticle matrix while the water soluble polyoxyethylene block forms a hydrophilic coating on the particle. Stealth nanoparticles may also be prepared by coating them with soluble polyoxyethylene or by using dialkyl polyoxyethylenes and phospholipids to make nanoparticles. The hydrophobic portions of these amphiphilic molecules, in the latter case, comprise the particle matrix. Stealth nanoparticles can increase the tumor accumulation and tumoricidal activity of anticancer drugs.

Nanoparticles can also be used as vaccine adjuvants. Antigens adsorbed onto the surface or entrapped in the matrix of, for example, polymethylmethacrylate nanoparticles, induce an enhanced immunological response. Polymethylmethacrylate nanoparticles containing an antigen may protect against challenge with the disease to a greater extent than the antigen alone or an alum preparation of the antigen. Decreasing particle size and increasing hydrophobicity may improve the adjuvancy of these particles. The particles offer a prolonged and controlled presentation of the antigen to the immune system.

Microparticles are generally injected either intraperitoneally, intramuscularly, subcutaneously, or directly to the target organ and, because of their large size (10-160 mm), are ideal for providing a sustained release depot of the drug. The active compound can be gradually released on erosion or by diffusion from the particles. The rate of release can be varied by any number of methods, such as by modifying polymer molecular weight, particle size, and also by controls on the nature of the polymer/copolymer.

Microparticles can be delivered to the target area by any method, including by direct injection into a target organ or solid tumor. In some cases, microparticles can be injected directly into a body cavity such as the peritoneum. The particular microparticulate technology used and the method of its administration will depend on the particular application.

Like nanoparticles, biodegradable microparticles, such as polylactic acid and polylactic acid co-glycolic acid microspheres, can also be used as immune adjuvants by providing a depot formulation of the antigen at the site of administration. The antigen is thus continually released to the antigen presenting cells. The same concept can be applied using microspheres where the active ingredient being released is a drug, as opposed to an antigen.

Nanoparticles and microparticles alike may be constructed from materials that impart additional desired qualities in the body. For example, particles can be constructed from, or include, materials that are paramagnetic. Such materials include, but are not limited to, cobalt, cobalt ferrite, cobalt nitride, cobalt oxide, cobalt-palladium, cobalt-platinum, iron, iron-gold, iron-chromium, iron nitride, iron oxide, iron-palladium, iron-platinum, manganese nitride, neodymium, neodymium-iron-boron, nickel, etc. Any compound that has been identified as being paramagnetic can be used to impart a paramagnetic quality to a particulate. Examples of methods for making these paramagnetic micro- or nanoparticles are known in the art, but include, for example, precipitation of a paramagnetic compound in the presence of polymer (nanoparticles), or by coating of a paramagnetic compound to the surface of a particle (nanoparticles and microparticles).

Nanoparticles can more generally be made from ceramics, including metal oxide ceramics such as titanium, zinc, aluminum, and iron oxides. Other materials include silicates, such as silicon oxide. Clays, including but not limited to, montmorillonite, a layered alumino-silicate, can also be used to make nanoparticles. Combination nanoparticles can include any combination, but often include a polymeric material to impart certain desired qualities.

Examples of methods for making nanoparticles are well known in the art. There are three main categories, generally including vapor condensation, chemical synthesis, and solid-state processes. Again, the particular method chosen will depend on the desired end product and the desired application.

The VEGF polypeptides of the invention can be delivered from a variety of implants, not all of which are nano- or microparticles. For example, other embodiments of the present invention comprise surgical structural support elements such as sutures, staples, clips, pins, trocars, chest tubes, foley catheters, and indwelling catheters. Other embodiments envisioned include surgical implants which do not necessarily serve a structurally supportive role, including but not limited to, pills, pellets, rods, wafers, discs, and tablets. The shape of dosage forms of the present invention is not limiting, and is preferably selected considering the needs of the application. For example, a surgical suture may be preferable in those instances in which a deep surgical incision in muscle or fascia has been made, and which needs to be closed with a structural element. Surgical staples or clips may be preferred in a similar situation, the selection preferably depending on the needs and wants of the practitioner. Alternatively, in other preferred embodiments, a shallow wound may require sterile adhesive strips, rather than sutures for closure. In such other preferred embodiments, an implant such as a rod, or several pellets, is preferably placed into the wound prior to closure with the sterile adhesive strips. Again, the choice of shape and embodiment is preferably based on the needs and desires of the practitioner. For example, for those applications in which flexibility is desired, a collection of pellets may be more preferable than a stiff rod. Alternatively, for closure of a surface skin wound in a flexible part of the body, a surgical suture according to the invention may be desirable. The size and shape is not considered limiting, and is preferably selected based on the wants and needs of the practitioner.

Other embodiments of the present invention include those that are placed on the exterior of the body, but by nature of their placement, allow intimate contact with a wound. Such embodiments include but are not limited to, bandages, surgical dressings, gauzes, and sterile adhesive strips. Applications of such embodiments include but are not limited to, the treatment of superficial surgical sites, such as that present after the removal of a skin cancer lesion, or a wart. Other embodiments according to this aspect of the invention include the treatment of burn tissue, which can require significant revascularization.

Materials for use in the manufacture of the present invention include both absorbable and nonabsorbable materials. Absorbable materials for use in the present invention include both synthetic and non-synthetic materials. Synthetic absorbable materials include, but are not limited to, polyglycolic acid, copolymers of lactide and glycolide, polydioxanone, polyglactin, poliglecaprone, polyglyconate, and polygluconate. Non-synthetic absorbable materials for use in the present invention include catgut, cargile membrane, fascia lata, collagen, and gelatin. Nonabsorbable materials for use in the present invention include both synthetic and non-synthetic materials. Synthetic nonabsorbable materials for use in the present invention include nylons, rayons, polyolefins, and polyesters. Non-synthetic nonabsorbable materials for use in the present invention include silk, dermal silk, cotton, and linen. The present invention may preferably comprise mixtures of absorbable and nonabsorbable materials, as well as mixtures of synthetic and non-synthetic materials.

The present invention may comprise a polymeric material. In one embodiment, the polymeric material is the sole structural constituent of the invention, such as in polymeric implants, or surgical sutures or staples. In another embodiment, the polymer is an adjunct to the invention, such as in silk sutures which are impregnated with a VEGF peptide, and which are coated with a polymer. In such an embodiment, the polymer preferably modifies the release of the peptide from the suture so as to achieve the desired result. In embodiments in which the polymeric material is the sole structural constituent of the invention, the invention is absorbed by the body, as VEGF is released over time. In other embodiments, the polymeric material is nonabsorbable and the VEGF is released over an extended period of time.

According to the present invention, and in accordance with the desired embodiment, the VEGF may be incorporated in any known manner. For example, in an embodiment in which VICRYL (polyglactin) sutures are used, the VEGF may be incorporated by dipping the suture in a solution of the VEGF, followed by drying. In other preferred embodiments in which other materials are used, the suture material may also be dipped into a solution of the VEGF. Alternatively, in other embodiments, the VEGF is mixed into a solution of the polymer prior to extruding and spinning into sutures, or prior to casting into implants. The choice for incorporation of the VEGF is preferably based on the desires and needs of the user.

In other embodiments, the VEGF may be incorporated into a device which becomes a permanent part of a body. For example, the VEGF may be incorporated into a cement for use in securing broken bones. In this case, the VEGF could be introduced at a site of injury, a broken bone, and released over a period of time. Even when the supply of VEGF is depleted, the bone cement would continue to serve its structural purpose. U.S. Pat. No. 4,373,217, to DRAENERT, discloses implantation formulations, and its entire disclosure is hereby incorporated by reference as though set forth in full herein. In another embodiment, the VEGF may be incorporated into a polymeric film which is used to coat a pin, which is used to secure a broken bone. Again, the VEGF would be released over time as the polymeric film dissolved, leaving the pin to hold the bone in place. A similar polymeric film containing a VEGF polypeptide could also be applied to a structural plate for implantation into a body.

Of course, while peptides, polypeptides, and proteins have been described as being delivered by conventional means, these substances can also be delivered through gene therapy. That is, these agents can be delivered to a subject by causing them to be expressed in the subject.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit, and scope of the invention. More specifically, it will be apparent that certain agents, which are both chemically and physiologically related, may be substituted for the agents described herein while the same or similar results would be achieved. All such similar substitutes and modifications apparent to those skilled in the art are deemed to be within the spirit, scope, and concept of the invention as defined by the appended claims.

The following examples are included to demonstrate specific embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

WORKING EXAMPLES

Example 1

Cloning of $VEGF_{205*}$ cDNA

The 5'-end of $VEGF_{205*}$ was amplified using an exon 2 forward primer (GAA GTC CCA TGA AGT GAT CAA G, SEQ ID NO: 7) and a reverse primer specific for the region downstream of exon 6 (TCC AGG GCA TTA GAC AGC A, SEQ ID NO: 8), using cDNA generated from total RNA isolated from FVB/N mouse lung tissue, yielding a product of 424 bp. To obtain the 3'-end, a primer spanning the exon 6 boundary into the immediate downstream region (TTC TGG AGC GTG TAC GTT, SEQ ID NO: 9) and a 3'-UTR reverse primer (AAA CCC TGA GGA GGC TCC TT, SEQ ID NO: 10). This was used to amplify a 250-bp product that was then gel-purified before re-amplification using a nested forward primer (TGG AGC GTG TAC GTT GGT, SEQ ID NO: 11). DNA fragments were cloned into pcDNA4/HisMax-TOPO and pCR2.1 (Invitrogen) and the DNA sequence of at least two clones was determined for each construct. The DNA fragments generated included overlap of cDNA sequence that was unique and not primer encoded.

Example 2

Expression, Purification, and Refolding of His-Tagged $VEGF_{120}$ and $VEGF_{205*}$ DNA fragments that encoded mature VEGF polypeptides were amplified by PCR using a common forward primer (GGC AGC CAT ATG GCA CCC ACG ACA GAA GGA, SEQ ID NO: 12) and specific reverse primers ($VEGF_{120}$ and $VEGF_{144}$, AGA CTC GAA TTC CTC ACC GCC TTG GCT TGT, SEQ ID NO: 13; for $VEGF_{205*}$, AGA CTC GAA TTC CAG GAA GGC TCC AAG GAA, SEQ ID NO: 14). Following amplification, the DNA fragments were cloned into pCR4-TOPO vector (Invitrogen) for verification by automated DNA sequencing. DNA fragments were subcloned into the NdeI-EcoRI restriction sites of pET-28a (Novagen, Madison, WI), which fuses an additional 21 amino acids and a His-Tag to the amino-terminus. Expression of recombinant protein was induced with 0.5 mM isopropyl β-D-1-thiogalactopyranoside in cultures of transformed E. coli BL21(DE3) cells (Stratagene, La Jolla, CA) grown to an optical density of 0.6 at 650 nm for 2 hr.

Bacterial cells were harvested, resuspended in 10 ml of TIN buffer (100 mM Tris0-HCl, pH 8.0, 5 mM imidazole, and 300 mM NaCl), and lysed by sonication. Inclusion bodies were washed with 40 mL of 2 M urea-TIN buffer and recombinant protein was extracted with 25 mL of 8 M urea-TIN buffer at 4° C. overnight. Clarified supernatant was applied to a 50-mL $Ni^{2+}$-Sepharose column (Amersham Pharmacia Biotech, Uppsala, Sweden), washed (60 mM imidazole), and eluted (120 mM imidazole). Recombinant protein was diluted to 90-140 ng/mL in 10 mM Tris-HCl, pH 8.5, 6 M urea, 0.1 M $NaH_2PO_4$, 20 mM dithiothreitol, 1 mM EDTA, dialyzed against 100 mM Tris-HCL, pH 8.5, 0.5 M guanidine hydrochloride, 2 mM EDTA, 5 mM cysteine, 1 mM cysteine overnight, which was followed by dialysis against 0.1 M acetic acid (24 h), and finally dialyzed against phosphate-buffered saline (PBS). Clarified protein was concentrated using Centriplus YM-10 (Millipore, Bedford, Mass.). Protein concentrations were estimated using the BIO-RAD Protein Assay (BIO-RAD, Hercules, Calif.) and verified by Commassie-blue staining of 600 ng of reduced VEGF proteins separated by SDS-PAGE.

Example 3

Western Blot Analysis of Recombinant VEGF Proteins

To confirm the identity of recombinant VEGF proteins, 200 ng of each recombinant protein was separated by SDS-PAGE (12% gel) and transferred to nitrocellulose membrane. Membranes were probed with 1:1000 dilution of polyclonal anti-mouse $VEGF_{164}$ (R&D Systems, Minneapolis, Minn.) followed by 1:5000 dilution of donkey anti-goat IgG-HRP (Jackson ImmunoResearch Laboratories, West Grove, Pa.) in 5% non-fat dried milk powder and 1% BSA. The signal was developed with ECL+plus Western Blotting Detection System (Amersham Pharmacia Biotech).

Example 4

Identification of a Novel Murine VEGF Alternative Splice Variant of 145 Amino Acids The comparative exon structures of four murine VEGF alternative splice variants, including the exon structure of $VEGF_{205*}$, is shown in FIG. 1A. In murine $VEGF_{205*}$, the 6 carboxyl-terminal amino acids that are present in the majority of VEGF isoforms of human, mouse, and rat, including $VEGF_{144}$, which is CDKPRR (SEQ ID NO: 15), is replaced with a unique 7-amino acid carboxyl-terminal end, YVGAAAV (SEQ ID NO: 16). (A comparison of these amino acid sequences is set forth in FIG. 6.) This new variant is referred to herein as $VEGF_{205*}$ to avoid confusion with the murine alternative splice variant, $VEGF_{144}$. The expression of a rarely expressed VEGF alternative splice variant, $VEGF_{206}$, which contains an extended exon 6 has been characterized in humans. In the present work, it was discovered that the DNA sequence of VEGF205* differs from the human $VEGF_{206}$ cDNA in that in $VEGF_{205*}$, exon 6 is extended by 61 bases and is spliced to a unique position 120 bases upstream of exon 8. Protein translation into exon 6b occurs as an extension defined as 6', which is the 61-bp insert containing a stop codon, which results in termination of protein synthesis within this exon and mature polypeptide produced by the VEGF205* consists of 145 amino acids.

Example 5

Production of Recombinant $VEGF_{120}$ and $VEGF_{205*}$

Recombinant His-tagged $VEGF_{120}$ and $VEGF_{205*}$ proteins were produced. $VEGF_{120}$ has been shown to induce both proliferation and migration of vascular endothelial cells, and was therefore generated as a His-tagged protein for functional comparison. Efficient dimerization of purified recombinant VEGF proteins was achieved and disulfide bonding within the proteins was reduced using β-mercaptoethanol (βME), which yielded a single polypeptide (FIG. 1B). $VEGF_{205*}$ migrated as two bands, which represent glycosylated and unglycosylated forms of the protein, as has been seen with other VEGF splice variants. Western blotting using anti-VEGF antibody confirmed that the purified proteins had identity to $VEGF_{120}$ and $VEGF_{205*}$ (FIG. 1C).

Alternative splicing of VEGF pre-mRNA results in production of alternative splice variants of VEGF that can exert distinctly different biological effects on vascular endothelial cells, including human vascular endothelial cells. It was previously demonstrated by the present inventor that VEGF alternative splice variants are expressed at specific times during tumor-associated angiogenesis. The specific alternative splice variants appear to differentially stimulate specific functions of endothelial cells and therefore dictate the final vascular architecture and the pattern of blood vessel organization within a tumor or tissue.

Here, we cloned and sequenced $VEGF_{205*}$ cDNA, which we had previously identified only as an mRNA produced in murine skin papillomas and carcinomas. The exon structure of $VEGF_{205*}$ includes exons 1-6, with exon 6 extended by 61 bases (exon 6b) and spliced to a new site 120 bases 5' of the exon 8 splice site. Protein translation of this open reading frame yielded a novel VEGF isoform of 145 amino acids. $VEGF_{205*}$ differs from murine $VEGF_{144}$ by only the carboxyl-terminus with the 6 amino acids CDKPRR (SEQ ID NO: 15) being replaced by a unique 7-amino acid carboxyl-terminus, YVGAAAV (SEQ ID NO: 16). Thus, the positively charged and potentially kinked carboxyl-terminus found in the majority of VEGF isoforms is replaced in the novel $VEGF_{205*}$ splice variant with hydrophobic amino acids.

FIG. 6 shows an amino acid alignment between several VEGF alternative splice variants, including $VEGF_{205*}$. Note that the sequences shown in FIG. 6 include signal sequences spanning 26 amino acids on the amino-terminus. Thus, $VEGF_{205*}$ is shown as being 171 total amino acids, including its 26-amino acid signal sequence. When the signal sequence is removed, the sequence is 145 amino acids.

We have shown that $VEGF_{205*}$ will phosphorylate the tyrosine residues of VEGFR-2 at tyrosine residues Y951 and Y1054/1059, will have less mitogenic activity than other VEGF transcripts such as $VEGF_{120}$ due to the lack of exon 6 but will induce migration and organization of vascular endothelial cells into tubes that are precursors of capillaries.

Although relatively new, the use of VEGF-based anti-angiogenesis therapies shows significant promise, when used alone or in combination with conventional therapies. In addition, peptides that have specificity for vascular endothelium are useful as diagnostic tools. In addition, these peptides also have utility in treating diseases in which either lack of appropriate vascular architecture has occurred due to delayed development or due to damage to the vasculature. As demonstrated by the identification of the inhibitory VEGF165b alternative splice variant by the laboratories of Bates and Harper (Woolard et al., Cancer Res. 2004 Nov. 1; 64(21): 7822-35; Cui et al., Am J Physiol Renal Physiol. 2004 April; 286(4):F767-73. Epub 2003 Nov. 25; and Bates et al., Cancer Res. 2002 Jul. 15; 62(14):4123-31), identifying or producing recombinant forms of novel VEGF splice variants with specific biological functions may advance the development of effective therapeutics and diagnostics. In addition, the novel polypeptides of this invention can be used to develop adjuvants to anti-tumor therapies. Further analysis of differing biological functions of VEGF isoforms could delineate the function of the VEGF domains and allow development of targeted therapeutic intervention.

Example 6

Figure 2:
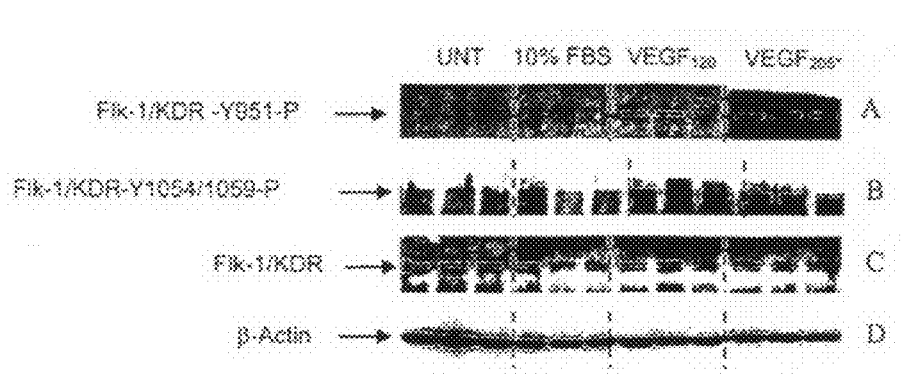
FIG. 2 shows the Western blot results from Example 6. Western blot is of HUVECs treated with 50 ng/ml VEGF$_{120}$, VEGF$_{205*}$, or 10% FBS for 2 min. Frame A shows levels of phospho-tyrosine VEGFR-2 at residue 951. Frame B shows levels of phospho-tyrosine VEGFR-2 at residue 1054/1059. Frame C shows total levels of VEGFR-2 ("Flk-1/KDR"). Frame D shows levels of β-actin used as the loading control.

$VEGF_{205*}$-Receptor Binding $VEGF_{205*}$ binds and signals through the VEGFR-2 (Flk-1/KDR) receptor and stimulates phosphorylation of Tyrosines at residues 951 and 1054/1059. Confluent cultures of HUVECs (85%) were serum and growth-factor starved for 6 hours and were left untreated (UNT), or treated with 50 ng/ml $VEGF_{120}$, $VEGF_{205*}$, or 10% FBS for 2 minutes. Aliquots of whole cell lysates (22 μg) were loaded into 8% SDS-PAGE gels, followed by immunoblotting with an antibody specific to phospho-tyrosine of VEGFR-2 receptor at residue 951 (FIG. 2A). The same samples were probed with anti-phospho-tyrosine antibody specific for residue 1054/1059 of VEGFR-2 (FIG. 2B). The same blots were then subsequently re-probed with anti-VEGFR-2 antibody to detect total levels of VEGFR-2 receptor (FIG. 2C). To confirm equal loading of samples, the same blot was stripped and re-probed for β-actin (FIG. 2D). The Western blots shown in FIG. 2 are representative of the experiments performed.

Example 7

$VEGF_{205*}$ Activates the AKT-1 Survival Pathway in Human Umbilical Vein Endothelial Cells (HUVECs)

HUVECs were plated at a density of $10^5$ cells per 100-mm dishes and cultured to reach 80% confluency in the presence of 10% serum. Cells were then exposed to serum starvation conditions by changing the media to 0% serum and growth factors. Six hours later, HUVECs were left untreated (UNT) or stimulated with either $VEGF_{120}$ (50 ng/mL) or $VEGF_{205*}$ (50 ng/mL) for the indicated time before harvest.

Figure 3:
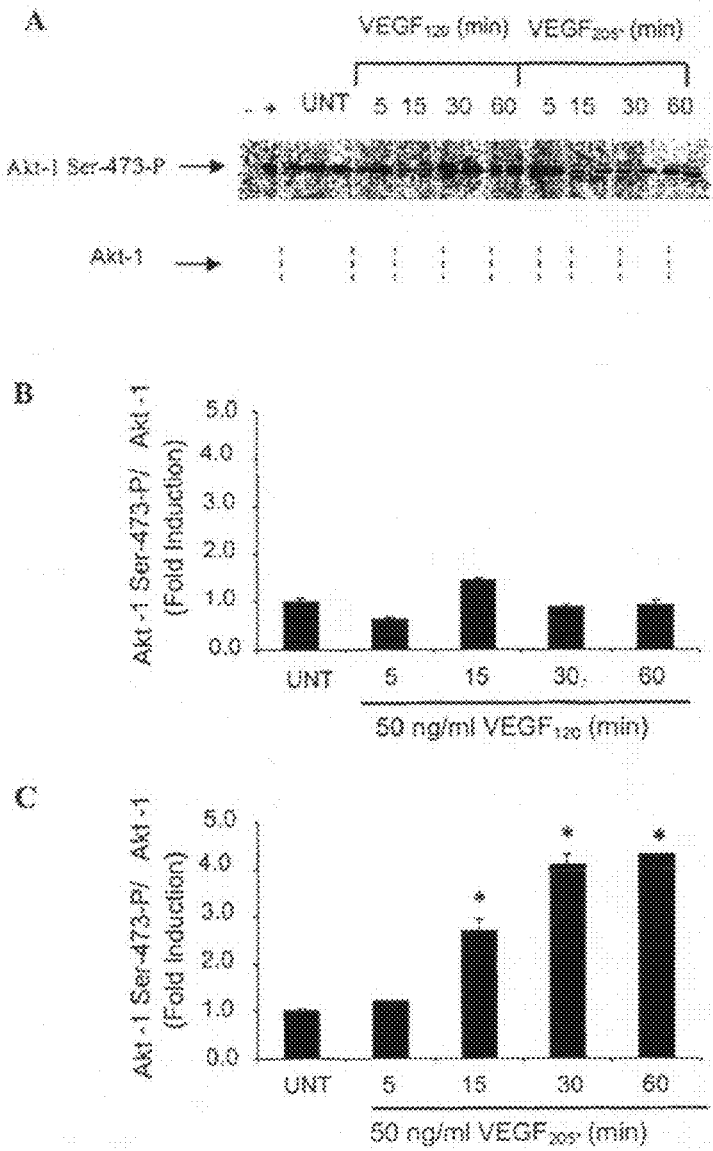
FIG. 3 shows a Western blot and densitometric analyses from work described in Example 7. Briefly, HUVECs were treated with either VEGF$_{120}$ (50 ng/ml) or VEGF$_{205*}$ (50 ng/ml) for the indicated time before analysis. Frame A shows a Western blot of anti-phospho-Akt-1 Ser473 in HUVECs. Data are expressed as fold increase with respect to unstimulated cells, with the ratio of phospho-Akt-1 Ser473 to the levels of Akt-1 expression (mean ±S.E.). Frames B and C show densitometric analysis of phospho-Akt-1 stimulated by VEGF$_{120}$ and VEGF$_{205*}$, respectively. Results are expressed as fold increase with respect to unstimulated cells. Data is expressed as ratio of phospho-Akt-1 Ser473 to level of Akt-1 (mean ±S.E.). *, p<0.05 versus unstimulated cells; **, p<0.01 versus unstimulated cells; @, p<0.05 versus VEGF$_{205*}$-treatment for 15 min.

FIG. 3A shows the results where an equal amount of whole cell lysates (22 ug) were loaded onto 8% SDS-PAGE gel, followed by immunoblotting with an antibody specific to phospho-Akt-1 at residue Ser473, which is used as a marker of activation of this survival-associated protein.

FIG. 3B shows a densitometric analysis of the immunoblot of Akt-1 phosphorylation in response to stimulation with $VEGF_{120}$. Results are expressed as fold-increase with respect to unstimulated cells. Data represent ratio of Akt-1 phosphorylation at Ser473 to the levels of Akt-1 expression and are expressed as mean ±standard error.

FIG. 3C shows a densitometric analysis of the immunoblot of Akt-1 phosphorylation in response to stimulation with $VEGF_{205*}$. Results are expressed as fold-increase with respect to unstimulated cells. Data represent ratio of Akt-1 phosphorylation at Ser473 to the levels of Akt-1 expression and expressed as mean ±standard error. *: $p<0.05$ versus unstimulated cells; **: $p<0.01$ versus unstimulated cells; @: $p<0.05$ versus $VEGF_{205*}$-stimulated for 15 minutes.

Example 8

Cardioprotective Effect of $VEGF_{205*}$

Rat fetal cardiomyocytes were exposed to doxorubicin (10 uM, $LD_{75}$ for myocyte killing) for 24 hours, in the presence of increasing concentrations of $VEGF_{120}$ or $VEGF_{205*}$. Doxorubicin is an important anti-neoplastic agent used against a variety of cancers, but the clinical utility is compromised by the development of dose-limiting cardiotoxicities. There has been no effective strategy for preventing this toxicity, and the mechanisms involved remain incompletely defined.

Cells were seeded in 96-well plates to confluence (15,000 cells/well), and myocyte survival after 24 hours was assessed using a crystal violet cell viability assay. Exposure to doxorubicin resulted in significant cell death. This toxicity was unaffected by co-treatment with $VEGF_{120}$, at concentrations as high as 25 ng/mL.

However, co-incubation with $VEGF_{205*}$ resulted in significant attenuation of doxorubicin-induced cytotoxicity, with significant protection seen at 10 ng/mL, and a doubling of myocyte densities at 25 ng/mL. These data do not appear to be explained by increased myocyte proliferation, as neither $VEGF_{120}$ or $VEGF_{205*}$ caused significantly increased cell counts over 24 hours compared to controls in the absence of doxorubicin.

These data provide the first evidence that VEGF may provide significant survival advantages to isolated myocytes in culture, suggesting that VEGF may be a new and effective agent in the prevention of doxorubicin-induced cardiotoxicity, and demonstrating the important differences and advantages that $VEGF_{205*}$ may possess relative to other VEGF splice variants. Furthermore, these data underscore the potent capacity of $VEGF_{205*}$ to promote cell survival under a variety of conditions.

Figure 4:
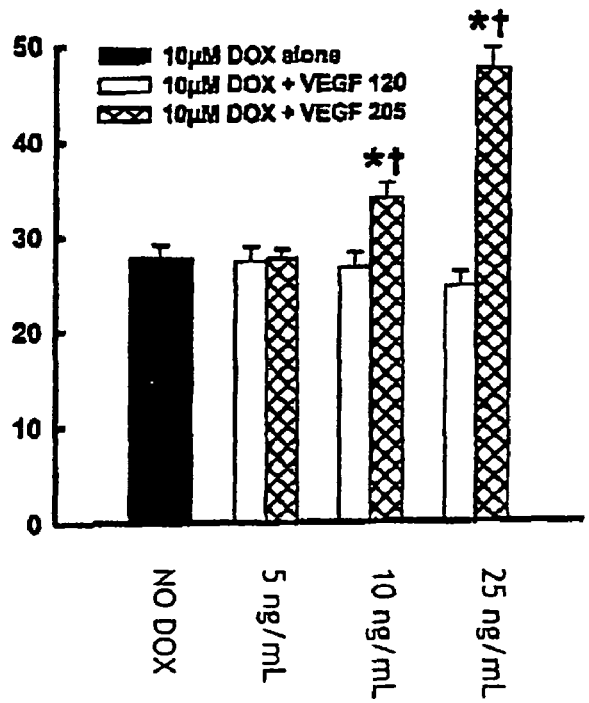
FIG. 4 is a graph showing the cardioprotective effect of VEGF$_{205*}$, as described in Example 8.

The results from these experiments are shown in FIG. 4.

Example 9

VEGF$_{205*}$ Stimulates the Protein Kinase B (IP3/Akt-1) Signaling Pathway

Figure 5:
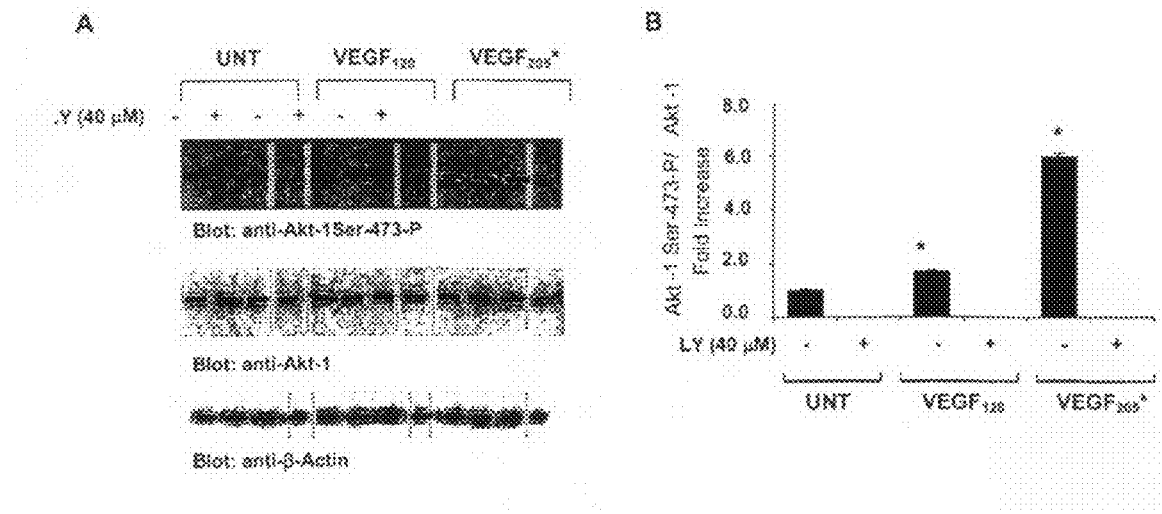
FIG. 5 shows a Western blot and densitometric analyses from work described in Example 9.
Figure 9:
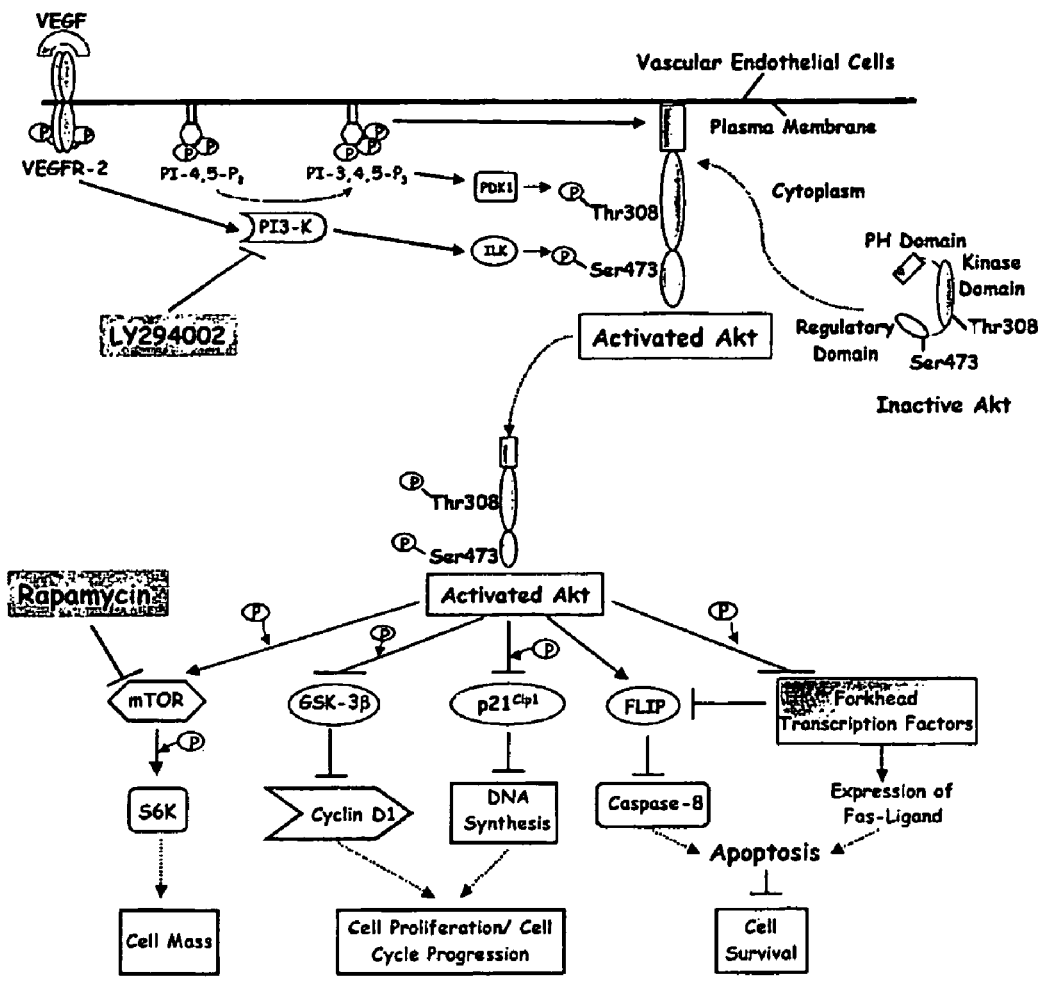
FIG. 9 diagrammatically illustrates how LY294002 affects the IP3-K signal pathway.

We have found that VEGF$_{205*}$ activates the IP3-K/Akt pathway, suggesting that it can selectively block apoptosis of cell populations involved in tumor-associated angiogenesis. As shown in FIG. 5, the novel murine VEGF splice variant VEGF$_{205*}$ (50 ng/ml), but not VEGF$_{120}$, led to a significant 3.5-fold increase (p<0.02) in Akt activation in human vascular endothelial cells. This response was measured by Western blot quantitation of Akt phosphorylation at Serine-473 residue using a specific anti-phospho-Akt-Ser473 antibody, which was inhibited by the specific IP3-K inhibitor LY294002. (FIG. 9 diagrammatically illustrates how LY294002 impacts the IP3-K signal pathway.) These results demonstrate that VEGF$_{205}$* selectively stimulates the IP3-K signal transduction pathway in vascular endothelial cells.

The results from these experiments are shown in FIG. 5.

Example 10

Effect of VEGF Variants on Wound Healing

VEGF$_{120}$, VEGF$_{144}$, VEGF$_{164}$, and VEGF$_{205*}$ were tested for their ability to promote wound healing. The studies were performed using human HUVECs treated with concentrations of recombinant VEGF$_{120}$, VEGF$_{144}$, VEGF$_{164}$, and VEGF$_{205*}$. The cells were grown to confluency and a standard-sized "wound" was created by removing a fixed area of cells. Measurement of proliferation and migration was then measured using light microscopy and digital image analysis. Experiments were performed in multi-well dishes, and the number of replicates for each experiment was at least 12.

Figure 10:
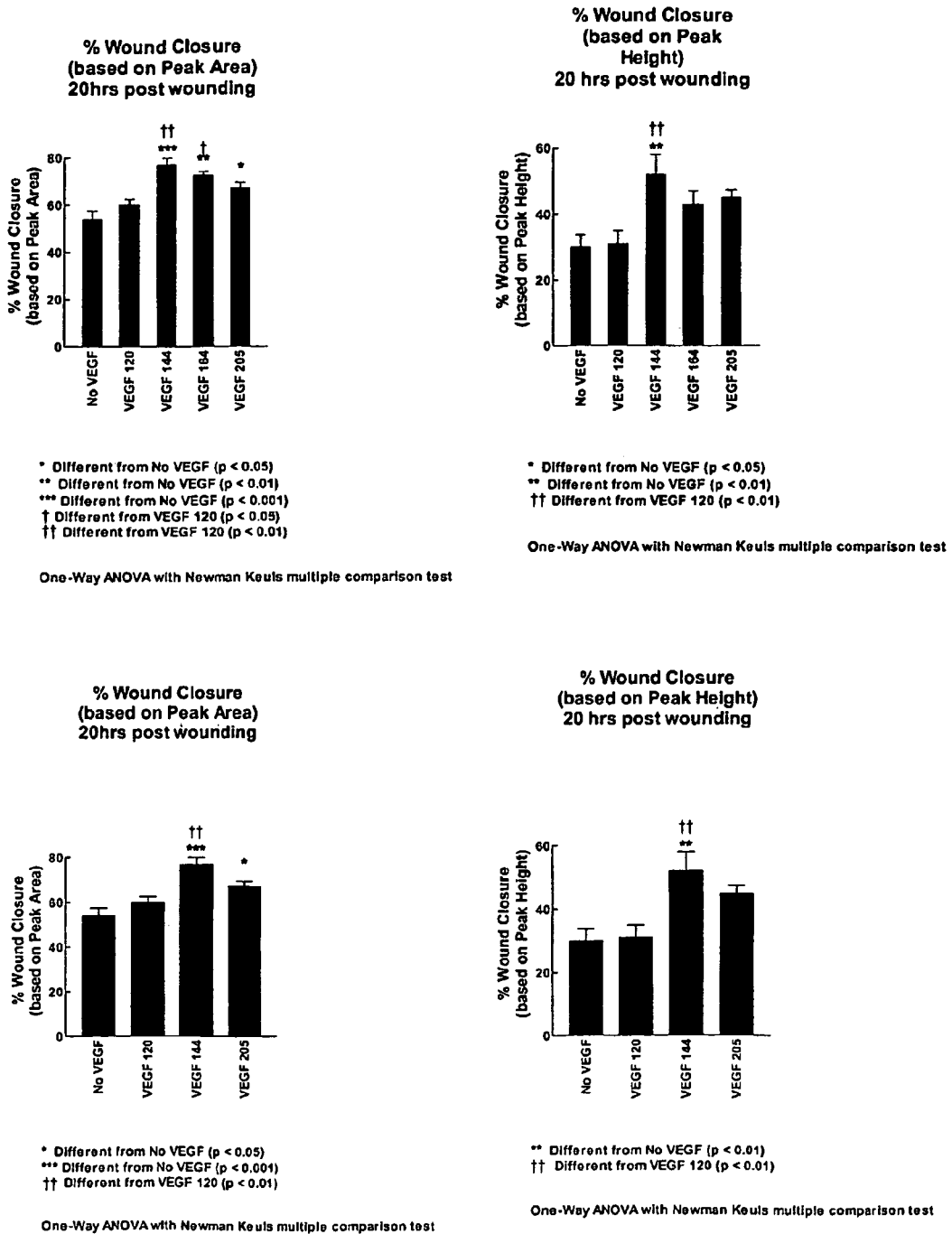
FIG. 10 illustrates the wound-healing effect of various VEGF variants, including VEGF$_{205*}$, as described in Example 10.

The results of these experiments are shown in FIG. 10.

Example 11

VEGF$_{205*}$-Induced Tubule Formation in HUVECs on Collagen-Coated Plates

HUVECs (4×10$^4$ cells/well) were plated on collagen-coated 96-well plates and treated for 30 hrs at 37° C. in the absence of serum and mitogenic factors with: A. 10% fetal calf serum; B. 50 ng/ml of recombinant VEGF$_{120}$; C. 50 ng/ml of recombinant VEGF$_{205*}$; and D. 50 ng/ml of recombinant VEGF$_{120}$ and 2 ng/ml VEGF$_{205*}$. Treatments were assayed in quadruplicate.

Example 12

Phorbol Esters Induce VEGF$_{205*}$-Expression in Murine Papillomas

The mRNA of VEGF$_{205*}$ is detectable as determined by RT-PCR (reverse transcriptase polymerase chair reaction) detection methods in highly vascularized tissues including heart, lung, liver, kidney and brain but was not detected in spleen, small and large intestine, ovary, stomach, lymph nodes and normal skin of Tg.AC transgenic mice that contain a Ha-ras oncogene within the lining epithelium but was not detectable in any normal tissues of the genetically inbred strain of mice, FVB/N, which is the background strain of mice used to generate the Tg.AC transgenic mice.

VEGF$_{205*}$ mRNA and protein was detectable in preneoplastic skin papillomas only in Tg.AC transgenic mice that formed at 12 weeks following 5 topical application of phorbol ester. VEGF$_{205*}$ mRNA and protein was detectable in squamous cell carcinomas found in both Tg.AC mice that are induced by 5 topical application of phorbol ester as well as formed by full thickness wounding of these mice. (Due to the presence of activated Ha-ras oncogene, these animals form tumors at the site of any injury). VEGF$_{205*}$ mRNA and protein was detectable only in squamous cell carcinomas isolated from FVB/N mice topical treatment with a single dose of the carcinogen 7,12-dimethylbenz[a]anthracene followed for 30 weeks by twice weekly topical treatment with phorbol ester.

Example 13

Comparative Proliferation of HUVECs Induced by VEGF$_{205*}$ and VEGF$_{120}$

Figure 11:
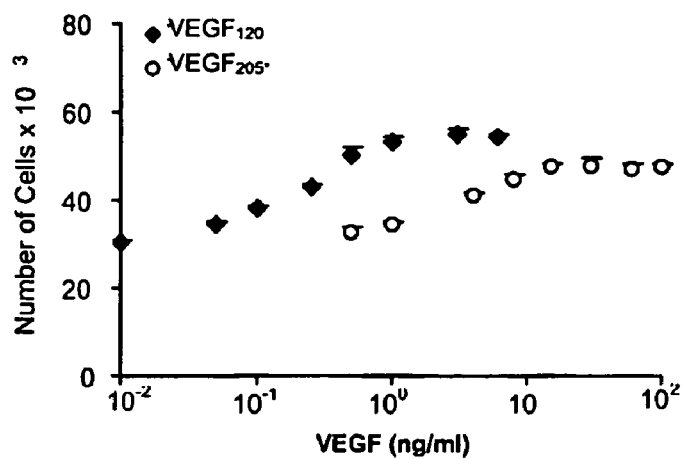
FIG. 11 shows comparative proliferation of HUVECs induced by VEGF$_{205*}$ and VEGF$_{120}$. HUVECs were treated with increasing concentration of VEGF$_{205*}$ or VEGF$_{120}$ as described below. The relative number of cells was quantified by Alamar blue dye. Data points represent the average ±S.E., with 6 replicates at each VEGF concentration.
Figure 12:
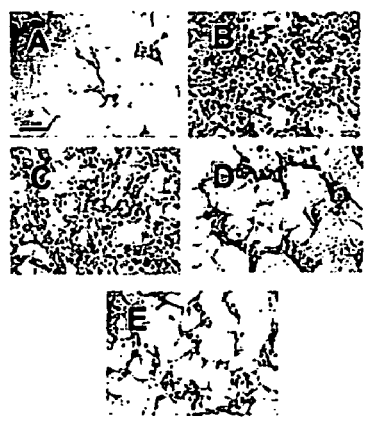
FIG. 12 shows how VEGF$_{205*}$ induces vessel-like structures in vitro. Briefly, HUVECs ($4 \times 10^4$ cells/well) were plated on collagen-coated 96-well plates and treated for 30 hrs at 37° C. in the absence of serum and mitogenic factors with: A. 10% fetal calf serum; B. 50 ng/ml of recombinant VEGF$_{120}$; C. 50 ng/ml of recombinant VEGF$_{205*}$; and D. 50 ng/ml of recombinant VEGF$_{120}$ and 2 ng/ml VEGF$_{205*}$. Treatments were assayed in quadruplicate.

HUVECs were treated with increasing concentration of VEGF$_{205*}$ or VEGF$_{120}$ as described under "Experimental Procedures". The relative number of cells was quantified by Alamar blue dye. Data points represent the average ±S.E., with 6 replicates at each VEGF concentration. The results are shown in FIG. 11.

Thus, to summarize, VEGF$_{205*}$ induces proliferation of cells, including HUVECs, and the induction of proliferation is the same as that observed with VEGF$_{144}$, but less than that observed for VEGF$_{120}$. VEGF$_{205*}$ also induces HUVECs to form tubules on collagen-coated plates and these tubules are more expansive than those induced by VEGF$_{120}$. VEGF$_{205*}$ also binds to VEGFR-2 (Flk-1/KDR) with an affinity equal to that of VEGF$_{144}$ but more than that of VEGF$_{120}$. Expression of VEGF$_{205*}$ is increased in murine papillomas using 12-o-tetradecanoylphorbol-13-acetate in Tg.AC mice, which carry the v-HA-ras transgene.

Example 14

VEGF$_{205*}$ Induces Survival Factors in Mouse Skin Cells

Antibodies directed against cytokeratin 15 were produced and were found to identify a specific population of presumptive stem cells that are located in a specific region of the hair follicle known as the bulge region (Ito, M., Kizawa, K., Hamada, K. and Cotsarelis, G. Differentiation 72:548-557, 2004). This area is an out-pouching of the outer root sheath of the hair follicle. The stem cells that express the K15 protein are multipotent in that their progeny can generate all of the cells within both the hair follicle as well as the epidermis in general. The K15+ stem cell population also co-express a stem cell marker that is present in bone marrow progenitor stem cells, which is CD34 (Trempus, C., Morris, R., Bortner, C., Cotsarelis, G., Faircloth, R., Reece, J. and Tennant, W. (2003) J. Invest. Dermatol. 120:501-511). Using immunochemical and immunofluorescence methods, we performed studies to identify the Akt survival pathway present in the skin stem cells that co-express K15 and CD34 and to determine the ability of VEGF205* to induce expression of pAkt in the stem cell population of cells in the skin.

Briefly, Sencar mice were injected subcutaneously into the dorsal epidermis with 2 ng, 5 ng, 10 ng, 20 ng, and 50 ng recombinant VEGF$_{205}$-protein. At 24 hrs, mice were euthanized, and skin was removed and evaluated for the presence of pAkt, as determined by immunofluorescence localization of anti-Akt-p-serine 473 combined with anti-K15 or anti-CD34 antibodies.

Double Immunochemical Staining Methods:

Serial sections of fixed, paraffin-embedded skin samples (4-mm) were cut and mounted onto microscope slides (SuperFrost/Plus, Fisher Scientific, Pittsburgh, Pa.). Tissues sections were then deparaffinized using Histo-Clear (National Diagonistics, Atlanta, Ga.), and rehydrated in a graded series of alcohol. Endogenous peroxidase activity was quenched for 20 min using 3% $H_2O_2$ in methanol. Samples were then subjected to antigen retrieval by steam heating for 15 min in 10 mM citrate buffer (pH 6.0). Sections were then blocked for 1 hr in 1% bovine serum albumin (BSA) (Sigma) and either 10% normal chicken serum or 10% normal goat serum (Vector Laboratories) in 1×TBST, pH 7.6 (Tris, 11.6 mM; Tris-HCl, 38 mM; NaCl, 150 mM; Tween 20, 0.05%). Bulge cells were double-stained for these following combinations: CD34 (red/membrane staining) and K15 (brown/cytoplasmic staining), either of CD34 (red/membrane staining) or K15 (red/cytoplasmic staining) and pAkt (brown/cytoplasmic staining), and either of CD34 or K15 (red/membrane staining) and PCNA (brown/nuclear staining). Tissue sections were incubated with either chicken polyclonal anti-keratin 15 (1:200 in 1% BSA in TBST, Covance, Berkley, Calif.) overnight at 4° C., or goat polyclonal anti-CD34 (1:150, Santa Cruz Biotechnology) for 1 hr at room temperature. Samples were then incubated for 20 min at room temperature with either of biotinylated goat anti-chicken IgG (1:200, Vector Laboratories) or biotinylated horse anti-goat IgG (1:200, Vector Laboratories). Slides were washed and incubated with the alkaline phosphatase-based ABC system (Vector Laboratories). The slides were then incubated with the chromagen Vector Red alkaline phosphatase substrate (Vector Laboratories). Using the chromagen Vector Red enabled us to visualize CD34 or K15 staining under both light and fluorescent microscopy as vector red substrate can be also visualized as a bright red fluorescent color under the fluorescein excitation filter. To stop the Vector Red development reaction, slides were washed with distilled water. Samples were then pre-treated with Avidin/Biotin blocking kit (Vector Laboratories) prior to incubation overnight at 4° C. with either rabbit polyclonal anti-PCNA (1:50, Santa Cruz Biotechnology) or rabbit polyclonal anti-phospho-Serine-473-Akt (1:50, Santa Cruz Biotechnology). Tissue sections were then incubated for 20 min with biotinylated goat anti-rabbit IgG (1:200, Vector Laboratories). Slides were then washed and incubated with the streptavidin horseradish peroxidase-based ABC reagent (Vector Laboratories), and color was developed using the chromagen 3,3-diaminobenzidine (DAB; Vector Laboratories). To stop the DAB development reaction, slides were washed with distilled water. Slides were then dehydrated, mounted, and subjected to fluorescence and digital photomicroscopy. Specificity of antibody binding was determined by incubation with only secondary antibodies.

Double Immunofluorescent Staining Methods:

Sections of fixed, paraffin-embedded skin samples (4-mm) were mounted onto glass sides (SuperFrost/Plus, Fischer Scientific, Pittsburgh, Pa.). Tissue sections were then deparaffinized using Histo-Clear (National Diagonistics, Atlanta, Ga.) and rehydrated in a graded series of alcohols. Antigen was unmasked by heating samples in 10 mM citrate buffer (pH 6.0) in a microwave oven. To reduce autofluorescence, sections were treated in 3 changes of freshly prepared solutions of sodium borohydride (NaBH4, 1 mg/ml in PBS, Sigma) for 10 min each. To block background staining, tissue sections were incubated for 30 min at room temperature with Image-iT™ FX Signal Enhancer (Molecular Probes, Eugene, Oreg.). Tissues sections were then incubated overnight at room temperature in a humidified chamber with both rabbit polyclonal anti-phospho-Serine-473-Akt-1 (1:50 in PBS, Santa Cruz Biotechnology) and goat polyclonal anti-CD34 (1:50 in PBS, Santa Cruz Biotechnology). Tissue sections were then incubated at room temperature in the dark for 1 hr with Alexa Fluor-647-conjugated donkey anti-goat (1:500 in PBS, Molecular Probes). Sections were washed in PBS, then incubated for 1 hr with Alexa Fluor-555-conjugated donkey anti-rabbit IgG (1:500 in PBS, Molecular Probes). Tissues were then washed in PBS, dehydrated, and mounted using VectaShield Mounting Medium (Vector Laboratories), which contains the DNA dye 4', 6-diamidino-2-phenylindole (DAPI) that fluoresces in the 405 nm (blue) range and specifically stains nucleated cells. Specificity of antibody binding was determined by incubation with only secondary antibodies followed by placement of coverslips using Vectashield with DAPI.

Digital and Confocal Microscopy:

Digital images of tissue sections were captured using a Diagnostic Instruments digital camera (Insight camera; 1600×1200 resolution) mounted on an Olympus research microscope. Images were then transferred to digital image analysis software (Image Pro Plus, Media Cybernetics, Silver Spring, Md.). Images were captured using a 40× objective using identical lighting and optical settings. Fluorescent images were obtained using a laser scanning confocal microscope (Zeiss LSM 510 Meta), with excitation wavelengths of 543 nm for Alexa Fluor-555 (green) fluorescence, 633 nm for Alexa Fluor-647 (red), and 405 nm for DAPI-associated (blue) fluorescence. The emission signal was observed using a set of band-pass filters. Images were obtained using 40× objective lens at identical settings of illumination.

Results

Using confocal microscopy and digital image analysis, we found that there was a dose-dependent increase in pAkt-serine 473 within the K15/CD34+ cell population which is located in the bulge region of hair follicles. Since this cell population has been identified as the putative stem cell population in the skin, these results suggest that $VEGF_{205*}$ serves as a skin stem cell survival factor.

PROPHETIC EXAMPLES

Figure 13:
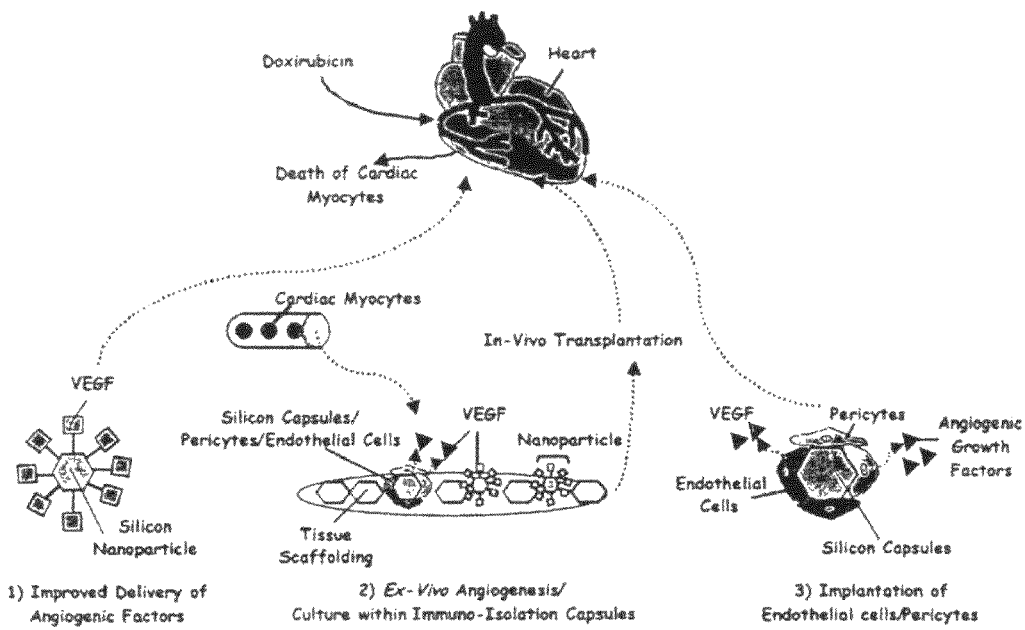
FIG. 13 shows a scheme of approaches to evaluate nanotechnology platforms.

This technology is combined with nanotechnology platforms to assess of the kinetics of cardiac and pulmonary tissue remodeling, which is dependent upon vascular endothelial growth factor (VEGF) proteins, and to selectively target VEGF proteins as a means of improved delivery of angiogenic factors to sites of injured cardiac and pulmonary tissues. FIG. 13 shows a schematic of approaches to evaluate nanotechnology platforms for their utility in providing selective protection against cardiac toxicity induced by Doxorubicin. This is an example of the types of approaches that can be used in accordance with this invention.

Example 15

$VEGF_{205*}$-Loaded Microparticles

Spherical silicon microparticles (1 micron in size), derivatized with polyethylene glycol molecules, are incubated with $VEGF_{205*}$ to load the VEGF onto the particles. The microparticles are manufactured as described in U.S. Patent Application Publication No. 2003/0114366. The microparticles are then applied to wound tissue to enhance the rate of wound healing.

Example 16

Use of Nanotechnology to Assess Tissue Remodeling

Specific nanotechnology platforms are evaluated as effective means to more precisely assess the kinetics of tissue remodeling that is dependent upon pro-angiogenic vascular endothelial growth factor (VEGF) proteins.

Particle Preparation:

Superparamagnetic particles are conjugated with recombinant $VEGF_{205*}$, using $VEGF_{120}$ as a comparative control protein. The effects of administration of anti-VEGF antibodies (R&D Systems, Minneapolis, Mich.) are assessed. Chitosan-lactic acid and porous silicon particles are similarly loaded with VEGF proteins for targeted delivery in addition to fluorescein for tracking in the tissues. Particles that offer the most optimal combination of overall size, chemistry, and payload capabilities are utilized.

Animal Models:

Murine model of Doxorubicin induced-cardiac damage:

CD-1 mice are injected intraperitoneally (i.p.) with weight-adjusted doses of doxorubicin (4 mg/kg) on a weekly basis for 6 weeks. Mice are sacrificed at intervals during injury induction and after completion of the injection protocol, as described previously (Weinstein et al., J. Pharmacol. Exp. Ther. 2000 July; 294(1):396-401; Mihm et al., Br J. Pharmacol. 2002 February; 135(3):581-8).

Murine model of Bleomycin-induced lung injury:

CD-1 mice are injected i.p. with weight-adjusted doses of bleomycin on a weekly basis for five weeks. Mice are sacrificed at intervals during induction of pulmonary injury and after completion of the injection protocol.

Hyperoxia-Induced Murine Lung Injury:

CD-1 mice are placed in an environment of 100% oxygen for 24 hours, generally a sub-lethal exposure, and sacrificed after 48 hours. Conjugated or loaded nanoparticles are administered intravenously during or post injury.

Assessments:

1. Delivery of these nanoparticles to specific targets (e.g., heart, lung) is tracked by magnetic resonance imagining in the case of superparamagnetic particles and by fluorescence microscopy in the case of labeled silicon and chitosan particles. The kinetics of cell-specific survival, proliferation, differentiation, and organization into new vessels at the target site are evaluated by direct microscopic visualization and imaging, i.e., digital imaging to assess the kinetics of organization of vascular endothelium into tubules as described above. Blood flow is evaluated during tissue remodeling based on EPR and MRI protocols.

2. Nanoscale particulates are used in conjunction with electron paramagnetic resonance imaging to assess and localize reactive oxygen and nitrogen intermediates produced during cardiac and pulmonary remodeling in vivo. These studies are performed in conjunction with assessment VEGF mRNA (Tober et al., Biochem Biophys Res Commun. 1998 Jun. 29; 247(3):644-53), HIF-1-alpha gene expression, immunochemical localization of 8-oxo-doxyguanosine DNA adducts as a marker for oxidative damage, and 3-nitrotyrosine as a measure of the presence of the labile intermediates derived from the interaction of nitric oxide and superoxide anion, i.e. peroxynitrite, as described previously (Weinstein et al., J. Pharmacol. Exp. Ther. 2000 July; 294(1):396-401; Mihm et al., Br J. Pharmacol. 2002 February; 135(3):581-8; and Robertson et al. Carcinogenesis. 1996 September; 17(9): 2053-9). To evaluate the angiogenesis in cardiac and pulmonary tissues, CD-31 is used as a marker for vascular endothelium, desmin is used to identify pericytes, and proliferating cell nuclear antigen (PCNA) is used to quantify proliferation of cells involved in cardiac and pulmonary vascular remodeling.

Further imaging instrumentation is developed to visualize and quantify kinetics and the extent of tissue repair associated angiogenesis and vascular remodeling: Methods are developed using intravital microscopy (IVM) in conjunction with our established methods for digital quantitative image analysis and confocal microscopy as a means to direct visualization of the effects of delivery of angiogenic growth factors on establishment of new vessels, tissue and vascular remodeling, as has been recently described using VEGF proteins in conjunction with IVM (Borgstrom et al. Anticancer Res. 1999 September-October; 19(5B):4203-14).

Also develop is use of the Xenogen system (located in the Ohio State University College of Veterinary Medicine), which allows real-time visualization of fluorescent or luminescent-based luciferase constructs that are present in live animals. This allows visualization of the ability of growth factors delivered using nanotechnology platforms to stimulate and/or inhibit angiogenesis/tissue remodeling in whole animals.

As an example: VEGF-coated nanoparticles would be injected into VEGFR-2-luciferase transgenic animals following cardiac or pulmonary injury. Such studies would allow quantitative assessment of tissue remodeling and repair-associated angiogenesis (Zhang et al., Blood. 2004 Jan. 15; 103 (2):617-26) and would also provide quantitative analysis of the effects of nanotechnology-based delivery of pro-angiogenic growth factors such as $VEGF_{205*}$. Using luciferase/fluorescent tagged systems (luc/eGFP/YFP), real time analysis of angiogenesis/vascular pathology can be performed at the level of cells, tissue, and whole animals, with the added benefit that the same animals can be followed over time.

Example 17

Co-Culture of Endothelial Cells and Pericytes Utilizing Tissue Scaffolding with Nano-Scale Features A method of co-culture of endothelial cells and pericytes utilizing tissue scaffolding with nano-scale features is developed for use in ex vivo angiogenesis studies and for culture within immunoisolation capsules for in vivo implantation.

A system of scaffolds with nanoscale architectural features is developed to allow co-culture of endothelial cells and pericytes. This permits studies to determine the interactive role of these cell types in vessel organization and stabilization during angiogenesis. Although numerous studies have been performed to evaluate the role of vascular endothelial cells during angiogenesis, studies are only now emerging on the essential role of pericytes early in the process of angiogenesis (Ozerdem et al., Angiogenesis. 2003; 6(3):241-9; Ortiz et al., Proc Natl Acad Sci USA. 2003 Jul. 8; 100(14):8407-11). This 3-dimensional scaffolding co-culture system allows culture of the combination of vascular endothelium and pericytes under normal conditions and under conditions of hypoxia and hyperoxia, which are known to induce significant differences in vascular remodeling.

Example 18

Silicon Capsules with Nanoengineered

Features for Culture and Implantation of Pericyte-Endothelial Cell Tissues This example describes the use of silicon capsules with nanoengineered features for culture and implantation of pericyte-endothelial cell tissues for use in delivery of endothelial growth factors to areas of heart and lung injury.

Based upon the optimal configuration of endothelial cell-pericyte culture scaffolds determined as described in Example 15, fully enclosed capsules are designed to allow implantation of the tissue cultures in the above-described murine models of injury. The capsules are constructed so that VEGF proteins and other smaller compounds are permitted to exit from the capsule, but that the capsule does not permit entry of immunoglobulins and other components of humoral immunity.

Capsules are implanted into animal models of heart and lung injury as per above. The activity of implants is assessed as a means to directly deliver pro-angiogenic growth factors or to deliver cells that produce these growth factors. The effect of these implants is assessed by evaluation of survival, proliferation, and organization of cells/remodeling of tissues, as described elsewhere in this document.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated or purified polypeptide comprising amino acids 27 through 171 of SEQ ID NO: 1.

2. A method of inducing migration and survival of vascular endothelial cells, comprising administering to the cells an effective amount of the polypeptide according to claim 1.

3. An implantable medical device or implant coated with a polypeptide according to claim 1.

4. The device or implant according to claim 3, wherein the device or implant is a suture.

5. An additive for cell culture medium comprising the polypeptide according to claim 1.

6. A cell culture medium comprising the polypeptide according to claim 1.

7. An isolated or purified polypeptide consisting of amino acids 27 through 171 of SEQ ID NO: 1.

8. An isolated or purified polypeptide comprising SEQ ID NO: 1.

* * * * *

SEQUENCE LISTING

<160> NUMBER OF SEQ ID NOS: 16

<210> SEQ ID NO 1
<211> LENGTH: 171
<212> TYPE: PRT
<213> ORGANISM: Mus sp.

<400> SEQUENCE: 1

Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
                20                  25                  30

Glu Gln Lys Ser His Glu Val Ile Lys Phe Met Asp Val Tyr Gln Arg
            35                  40                  45

Ser Tyr Cys Arg Pro Ile Glu Thr Leu Val Asp Ile Phe Gln Glu Tyr
        50                  55                  60

Pro Asp Glu Ile Glu Tyr Ile Phe Lys Pro Ser Cys Val Pro Leu Met
65                  70                  75                  80

Arg Cys Ala Gly Cys Cys Asn Asp Glu Ala Leu Glu Cys Val Pro Thr
                85                  90                  95

Ser Glu Ser Asn Ile Thr Met Gln Ile Met Arg Ile Lys Pro His Gln
            100                 105                 110

Ser Gln His Ile Gly Glu Met Ser Phe Leu Gln His Ser Arg Cys Glu
        115                 120                 125

Cys Arg Pro Lys Lys Asp Arg Thr Lys Pro Glu Lys Lys Ser Val Arg
    130                 135                 140

Gly Lys Gly Lys Gly Gln Lys Arg Lys Arg Lys Lys Ser Arg Phe Lys
145                 150                 155                 160

Ser Trp Ser Val Tyr Val Gly Ala Ala Ala Val
                165                 170

<210> SEQ ID NO 2
<211> LENGTH: 214
<212> TYPE: PRT
<213> ORGANISM: Mus sp.

<400> SEQUENCE: 2

Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
                20                  25                  30

Glu Gln Lys Ser His Glu Val Ile Lys Phe Met Asp Val Tyr Gln Arg
            35                  40                  45

Ser Tyr Cys Arg Pro Ile Glu Thr Leu Val Asp Ile Phe Gln Glu Tyr

```
                50                    55                     60
Pro Asp Glu Ile Glu Tyr Ile Phe Lys Pro Ser Cys Val Pro Leu Met
 65                  70                  75                  80

Arg Cys Ala Gly Cys Cys Asn Asp Glu Ala Leu Glu Cys Val Pro Thr
                     85                  90                  95

Ser Glu Ser Asn Ile Thr Met Gln Ile Met Arg Ile Lys Pro His Gln
                100                 105                 110

Ser Gln His Ile Gly Glu Met Ser Phe Leu Gln His Ser Arg Cys Glu
            115                 120                 125

Cys Arg Pro Lys Lys Asp Arg Thr Lys Pro Glu Lys Lys Ser Val Arg
130                 135                 140

Gly Lys Gly Lys Gly Gln Lys Arg Lys Arg Lys Ser Arg Phe Lys
145                 150                 155                 160

Ser Trp Ser Val His Cys Glu Pro Cys Ser Glu Arg Arg Lys His Leu
                165                 170                 175

Phe Val Gln Asp Pro Gln Thr Cys Lys Cys Ser Cys Lys Asn Thr Asp
            180                 185                 190

Ser Arg Cys Lys Ala Arg Gln Leu Glu Leu Asn Glu Arg Thr Cys Arg
        195                 200                 205

Cys Asp Lys Pro Arg Arg
210

<210> SEQ ID NO 3
<211> LENGTH: 190
<212> TYPE: PRT
<213> ORGANISM: Mus sp.

<400> SEQUENCE: 3

Met Asn Phe Leu Leu Ser Trp Val His Trp Thr Leu Ala Leu Leu Leu
 1               5                  10                  15

Tyr Leu His His Ala Lys Trp Ser Gln Ala Ala Pro Thr Thr Glu Gly
                20                  25                  30

Glu Gln Lys Ser His Glu Val Ile Lys Phe Met Asp Val Tyr Gln Arg
            35                  40                  45

Ser Tyr Cys Arg Pro Ile Glu Thr Leu Val Asp Ile Phe Gln Glu Tyr
        50                  55                  60

Pro Asp Glu Ile Glu Tyr Ile Phe Lys Pro Ser Cys Val Pro Leu Met
 65                  70                  75                  80

Arg Cys Ala Gly Cys Cys Asn Asp Glu Ala Leu Glu Cys Val Pro Thr
                     85                  90                  95

Ser Glu Ser Asn Ile Thr Met Gln Ile Met Arg Ile Lys Pro His Gln
                100                 105                 110

Ser Gln His Ile Gly Glu Met Ser Phe Leu Gln His Ser Arg Cys Glu
            115                 120                 125

Cys Arg Pro Lys Lys Asp Arg Thr Lys Pro Glu Asn His Cys Glu Pro
130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190

<210> SEQ ID NO 4
<211> LENGTH: 170
<212> TYPE: PRT
```

<213> ORGANISM: Mus sp.

<400> SEQUENCE: 4

```
Met Asn Phe Leu Leu Ser Trp Val His Trp Thr Leu Ala Leu Leu Leu
 1               5                  10                  15
Tyr Leu His His Ala Lys Trp Ser Gln Ala Ala Pro Thr Thr Glu Gly
                20                  25                  30
Glu Gln Lys Ser His Glu Val Ile Lys Phe Met Asp Val Tyr Gln Arg
            35                  40                  45
Ser Tyr Cys Arg Pro Ile Glu Thr Leu Val Asp Ile Phe Gln Glu Tyr
        50                  55                  60
Pro Asp Glu Ile Glu Tyr Ile Phe Lys Pro Ser Cys Val Pro Leu Met
 65                  70                  75                  80
Arg Cys Ala Gly Cys Cys Asn Asp Glu Ala Leu Glu Cys Val Pro Thr
                85                  90                  95
Ser Glu Ser Asn Ile Thr Met Gln Ile Met Arg Ile Lys Pro His Gln
               100                 105                 110
Ser Gln His Ile Gly Glu Met Ser Phe Leu Gln His Ser Arg Cys Glu
           115                 120                 125
Cys Arg Pro Lys Lys Asp Arg Thr Lys Pro Glu Lys Lys Ser Val Arg
       130                 135                 140
Gly Lys Gly Lys Gly Gln Lys Arg Lys Arg Lys Lys Ser Arg Phe Lys
145                 150                 155                 160
Ser Trp Ser Val Cys Asp Lys Pro Arg Arg
                165                 170
```

<210> SEQ ID NO 5
<211> LENGTH: 146
<212> TYPE: PRT
<213> ORGANISM: Mus sp.

<400> SEQUENCE: 5

```
Met Asn Phe Leu Leu Ser Trp Val His Trp Thr Leu Ala Leu Leu Leu
 1               5                  10                  15
Tyr Leu His His Ala Lys Trp Ser Gln Ala Ala Pro Thr Thr Glu Gly
                20                  25                  30
Glu Gln Lys Ser His Glu Val Ile Lys Phe Met Asp Val Tyr Gln Arg
            35                  40                  45
Ser Tyr Cys Arg Pro Ile Glu Thr Leu Val Asp Ile Phe Gln Glu Tyr
        50                  55                  60
Pro Asp Glu Ile Glu Tyr Ile Phe Lys Pro Ser Cys Val Pro Leu Met
 65                  70                  75                  80
Arg Cys Ala Gly Cys Cys Asn Asp Glu Ala Leu Glu Cys Val Pro Thr
                85                  90                  95
Ser Glu Ser Asn Ile Thr Met Gln Ile Met Arg Ile Lys Pro His Gln
               100                 105                 110
Ser Gln His Ile Gly Glu Met Ser Phe Leu Gln His Ser Arg Cys Glu
           115                 120                 125
Cys Arg Pro Lys Lys Asp Arg Thr Lys Pro Glu Lys Cys Asp Lys Pro
       130                 135                 140
Arg Arg
145
```

<210> SEQ ID NO 6
<211> LENGTH: 522
<212> TYPE: DNA
<213> ORGANISM: Mus sp.

```
<220> FEATURE:
<221> NAME/KEY: CDS
<222> LOCATION: (1)..(513)

<400> SEQUENCE: 6 atg aac ttt ctg ctc tct tgg gtg cac tgg acc cag gct tta ctg ctg      48
Met Asn Phe Leu Leu Ser Trp Val His Trp Thr Gln Ala Leu Leu Leu
1               5                   10                  15 tac ctc cac cat gcc aag tgg tcc cag gct gca ccc acg aca gaa gga      96
Tyr Leu His His Ala Lys Trp Ser Gln Ala Ala Pro Thr Thr Glu Gly
            20                  25                  30 gag cag aag tcc cat gaa gtg atc aag ttc atg gat gtc tac cag cga     144
Glu Gln Lys Ser His Glu Val Ile Lys Phe Met Asp Val Tyr Gln Arg
        35                  40                  45 agc tac tgc cgt ccg att gag acc ctg gtg gac atc ttc cag gag tac     192
Ser Tyr Cys Arg Pro Ile Glu Thr Leu Val Asp Ile Phe Gln Glu Tyr
    50                  55                  60 ccc gac gag ata gag tac atc ttc aag ccg tcc tgt gtg ccg ctg atg     240
Pro Asp Glu Ile Glu Tyr Ile Phe Lys Pro Ser Cys Val Pro Leu Met
65                  70                  75                  80 cgc tgt gca ggc tgc tgt aac gat gaa gcc ctg gag tgc gtc ccc acg     288
Arg Cys Ala Gly Cys Cys Asn Asp Glu Ala Leu Glu Cys Val Pro Thr
                85                  90                  95 tca gag agc aac atc acc atg cag atc atg cgg atc aaa cct cac caa     336
Ser Glu Ser Asn Ile Thr Met Gln Ile Met Arg Ile Lys Pro His Gln
            100                 105                 110 agc cag cac ata gga gag atg agc ttc cta cag cac agc aga tgt gaa     384
Ser Gln His Ile Gly Glu Met Ser Phe Leu Gln His Ser Arg Cys Glu
        115                 120                 125 tgc aga cca aag aaa gac aga aca aag cca gaa aaa aaa tca gtt cga     432
Cys Arg Pro Lys Lys Asp Arg Thr Lys Pro Glu Lys Lys Ser Val Arg
    130                 135                 140 gga aag gga aag ggt caa aaa cga aag cgc aag aaa tcc cgg ttt aaa     480
Gly Lys Gly Lys Gly Gln Lys Arg Lys Arg Lys Lys Ser Arg Phe Lys
145                 150                 155                 160 tcc tgg agc gtg tac gtt ggt gcc gct gct gtc taattcctt              522
Ser Trp Ser Val Tyr Val Gly Ala Ala Ala Val
                165                 170

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaagtcccat gaagtgatca ag                                             22

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tccagggcat tagacagca                                                 19

<210> SEQ ID NO 9
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 9
ttctggagcg tgtacgtt                                                        18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaccctgag gaggctcctt                                                      20

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggagcgtgt acgttggt                                                        18

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcagccata tggcacccac gacagaagga                                           30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agactcgaat tcctcaccgc cttggcttgt                                           30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agactcgaat tccaggaagg ctccaaggaa                                           30

<210> SEQ ID NO 15
<211> LENGTH: 6
<212> TYPE: PRT
<213> ORGANISM: Mus sp.
```

```
-continued

<400> SEQUENCE: 15

Cys Asp Lys Pro Arg Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 16

Tyr Val Gly Ala Ala Ala Val
1               5
```